United States Patent
Fukunaga et al.

(10) Patent No.: US 10,683,266 B2
(45) Date of Patent: Jun. 16, 2020

(54) SULFONIUM SALT, PHOTOACID GENERATOR, PHOTOCURABLE COMPOSITION, AND CURED PRODUCT THEREOF

(71) Applicant: SAN-APRO LTD., Kyoto-shi, Kyoto (JP)

(72) Inventors: Noriya Fukunaga, Kyoto (JP); Yusaku Takashima, Kyoto (JP)

(73) Assignee: SAN APRO LTD., Kyoto-shi, Kyoto (JP)

( * ) Notice: Subject to any disclaimer, the term of this patent is extended or adjusted under 35 U.S.C. 154(b) by 0 days.

(21) Appl. No.: 16/303,273

(22) PCT Filed: Jun. 12, 2017

(86) PCT No.: PCT/JP2017/021601
§ 371 (c)(1),
(2) Date: Nov. 20, 2018

(87) PCT Pub. No.: WO2018/003470
PCT Pub. Date: Jan. 4, 2018

(65) Prior Publication Data
US 2019/0300476 A1 Oct. 3, 2019

(30) Foreign Application Priority Data
Jun. 29, 2016 (JP) .................... 2016-128396

(51) Int. Cl.
*C08F 2/46* (2006.01)
*C08F 2/50* (2006.01)
(Continued)

(52) U.S. Cl.
CPC .......... *C07C 381/12* (2013.01); *C07D 335/16* (2013.01); *C07F 5/00* (2013.01);
(Continued)

(58) Field of Classification Search
CPC ........ C07C 381/12; C08K 5/372; C08K 5/45; C08K 5/56; C07F 7/0841; C07F 7/08; C07F 5/00; C07D 335/16; C08G 59/4064; C08G 59/68
USPC ................. 522/31, 6, 189, 184, 1, 71; 520/1
See application file for complete search history.

(56) References Cited
U.S. PATENT DOCUMENTS
4,069,054 A 1/1978 Smith
4,394,403 A 7/1983 Smith
(Continued)

FOREIGN PATENT DOCUMENTS
CA 1274646 A 9/1990
EP 203829 A2 12/1986
(Continued)

OTHER PUBLICATIONS
Ikeda et al, JP 2013-043864 Machine Translation, Mar. 4, 2013 (Year: 2013).*
(Continued)

*Primary Examiner* — Jessica Whiteley
(74) *Attorney, Agent, or Firm* — Westerman, Hattori, Daniels & Adrian, LLP

(57) ABSTRACT
A sulfonium salt is formed of a sulfonium cation selected from a group indicated by general formulas (1), (2), and (3) and a gallate anion represented by formula (a). A photoacid generator is characterized in that said sulfonium salt is contained therein. An energy-ray curable composition contains the acid generator and a cationic polymerizable compound. A cured product is formed by curing these substances.

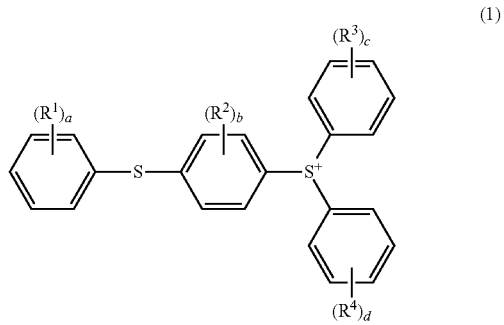

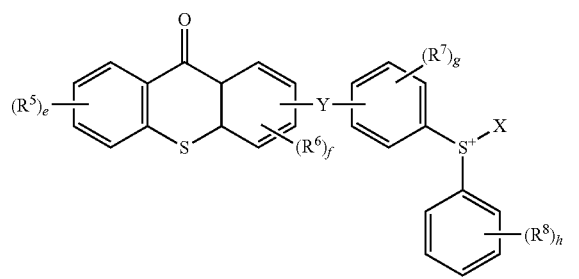

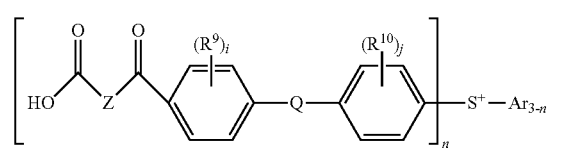

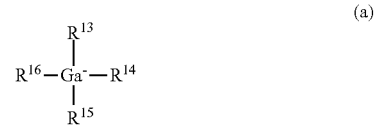

16 Claims, No Drawings

(51) Int. Cl.

| | | |
|---|---|---|
| *C08G 61/04* | (2006.01) | |
| *C07C 381/12* | (2006.01) | |
| *C07D 335/16* | (2006.01) | |
| *C07F 5/00* | (2006.01) | |
| *C07F 7/08* | (2006.01) | |
| *C08G 59/40* | (2006.01) | |
| *C08K 5/372* | (2006.01) | |
| *C08K 5/45* | (2006.01) | |
| *C08K 5/56* | (2006.01) | |
| *C08G 59/68* | (2006.01) | |
| *C09K 3/00* | (2006.01) | |

(52) U.S. Cl.
CPC ............... *C07F 7/08* (2013.01); *C07F 7/081* (2013.01); *C08G 59/4064* (2013.01); *C08G 59/68* (2013.01); *C08K 5/372* (2013.01); *C08K 5/45* (2013.01); *C08K 5/56* (2013.01); *C09K 3/00* (2013.01)

(56) References Cited

U.S. PATENT DOCUMENTS

| | | | |
|---|---|---|---|
| 4,450,360 A | | 5/1984 | Crivello et al. |
| 4,576,999 A | | 3/1986 | Eckberg |
| 4,640,967 A | | 2/1987 | Eckberg |
| 6,166,233 A | * | 12/2000 | Neckers .................... C07F 5/00 522/25 |
| 2007/0083060 A1 | | 4/2007 | Sumino et al. |

FOREIGN PATENT DOCUMENTS

| | | | |
|---|---|---|---|
| JP | 50-151997 A | | 12/1975 |
| JP | 50-158680 A | | 12/1975 |
| JP | 2-178303 A | | 7/1990 |
| JP | 2000-66385 A | | 3/2000 |
| JP | 2001-270990 A | | 10/2001 |
| JP | 2001-294570 A | | 10/2001 |
| JP | 2001-354669 A | | 12/2001 |
| JP | 2002-193925 A | | 7/2002 |
| JP | 2011-102269 A | | 5/2011 |
| JP | 2011-162471 A | | 8/2011 |
| JP | 2013043864 | * | 3/2013 |
| JP | 2014-201555 A | | 10/2014 |
| JP | 2014201555 | * | 10/2014 |
| WO | 2005/037778 A1 | | 4/2005 |
| WO | 2005/116038 A1 | | 12/2005 |
| WO | 2009/136482 A1 | | 11/2009 |
| WO | 2014/061062 A1 | | 4/2014 |
| WO | 2017/038379 A1 | | 3/2017 |

OTHER PUBLICATIONS

Suzuki et al, JP 2014/201555 Machine Translation, Oct. 27, 2014 (Year: 2014).*

International Search Report dated Sep. 5, 2017, issued in counterpart application No. PCT/JP2017/021601 (2 pages).

* cited by examiner

SULFONIUM SALT, PHOTOACID GENERATOR, PHOTOCURABLE COMPOSITION, AND CURED PRODUCT THEREOF

TECHNICAL FIELD

The present invention firstly relates to a sulfonium salt, and secondly relates to a photoacid generator, more specifically, a photoacid generator containing a specific sulfonium salt suitable for curing a cationic polymerizable compound by the action of an active energy ray such as light, an electron beam, or an X-ray.

The present invention thirdly relates to an energy ray-curable composition for members that are required to have optical properties, the composition containing the photoacid generator; and a cured product obtained by curing the same.

BACKGROUND ART

Onium salts such as iodonium and sulfonium salts have been heretofore known as cationic polymerization initiators for curing a cationic polymerizable compound such as an epoxy compound by application of heat, light or an active energy ray such as an electron beam (see Patent Documents 1 to 10).

In addition, since such an onium salt generates an acid by application of heat or an active energy ray, the onium salt is also referred to as an acid generator, and also used for resists and photosensitive materials (Patent Documents 11 to 13).

Incidentally, although cationic polymerization initiators (acid generators) described in these specifications contain $BF_4^-$, $PF_6^-$, $AsF_6^-$, or $SbF_6^-$ as an anion, curing performance of cationic polymerizable compound and crosslinking reaction performance varies with the kind of an anion and these performances are improved in an ascending order of $BF_4^-<PF_6^-<AsF_6^-<SbF_6^-$. However, applications of cationic polymerization initiators (acid generators) containing $AsF_6^-$ or $SbF_6^-$ which have good polymerization performance and crosslinking reaction performance are limited from a toxicity problem of As or Sb, and only an $SbF_6^-$ salt is used in a limited field such as photofabrication. On that account, although a $PF_6^-$ salt being poor in the polymerization performance and crosslinking reaction performance by acid catalyst is generally utilized, for example, in order to attain a curing rate almost comparable to that of an $SbF_6^-$ salt, since the $PF_6^-$ salt in an amount being nearly ten times the amount of the $SbF_6^-$ salt needs to be added and the remaining amount of an unreacted initiator (acid generator), a solvent used as necessary for dissolving the initiator (acid generator), or a decomposition product of the initiator is increased, there are problems that physical properties of a cured material are impaired, and moreover, a base material, facilities, and the like are liable to be corroded because of an increased amount of HF produced as a by-product by decomposition of the initiator. As such, a cationic polymerization initiator that is free from a toxic metal and has a cationic polymerization-initiating ability comparable to that of an $SbF_6^-$ salt has been strongly required.

In members that are required to have optical properties, such as displays, optical waveguides and optical lenses, importance is placed on transparency of cured products cured by application of heat, light or irradiation with an active energy ray such as an electron beam, and transparency of cured products after a heat resistance test and after a humidity resistance test. In addition, applications requiring corrosion resistance to a remaining strong acid include members such as paint compositions, coating agents, ink compositions, inkjet ink compositions, resist films, liquid resists, negative resists, MEMS resists, negative photosensitive materials, various adhesives, molding materials, casting materials, putty materials, glass fiber impregnating agents, fillers, sealing agents, sealants, optical semiconductor (LED) sealants, optical waveguide materials, nano-imprint materials, stereolithography materials, micro-stereolithography materials, and ACF (anisotropic conductive films).

The present inventors have proposed a fluorinated alkylphosphonic acid onium salt-based acid generator (Patent Document 14) as a cationic polymerization initiator (acid generator) which does not contain a toxic metal, and has cationic polymerization performance and crosslinking reaction performance comparable to those of a $SbF_6^-$ salt. However, a cured product including the acid generator has the problem that transparency is deteriorated particularly after a heat resistance test, and application of the acid generator to the above-mentioned members that are required to have optical properties has not progressed.

In addition, an onium salt having tetrakis(pentafluorophenyl)borate as an anion (Patent Document 15) is known as a cationic polymerization initiator (acid generator) which does not contain a toxic metal, and has cationic polymerization performance and crosslinking reaction performance comparable to those of a $SbF_6^-$ salt. However, a cured product including the acid generator has the problem that transparency is deteriorated because $HB(C_6F_5)_4$ as a strong acid remaining particularly after a heat resistance test causes corrosion and coloring of a resin etc., and application of the acid generator to the above-mentioned members that are required to have optical properties has not progressed.

PRIOR ART DOCUMENT

Patent Documents

Patent Document 1: Japanese Patent Application Laid-Open (JP-A) No. 50-151997
Patent Document 2: JP-A No. 50-158680
Patent Document 3: JP-A No. 02-178303
Patent Document 4: JP-A No. 02-178303
Patent Document 5: U.S. Pat. No. 4,069,054
Patent Document 6: U.S. Pat. No. 4,450,360
Patent Document 7: U.S. Pat. No. 4,576,999
Patent Document 8: U.S. Pat. No. 4,640,967
Patent Document 9: Canada Patent No. 1274646
Patent Document 10: European Patent Application Publication No. 203829
Patent Document 11: JP-A No. 2002-193925
Patent Document 12: JP-A No. 2001-354669
Patent Document 13: JP-A No. 2001-294570
Patent Document 14: WO2005-116038
Patent Document 15: JP-A No. 2000-66385

SUMMARY OF THE INVENTION

Problems to be Solved by the Invention

In view of the above-mentioned background, an object of the present invention is to provide a sulfonium salt which does not contain a toxic metal, has cationic polymerization performance and crosslinking reaction performance equivalent to or higher than those of tetrakis(pentafluorophenyl) borate salt; a photoacid generator characterized in that said sulfonium salt is contained therein; an energy ray-curable composition including the photoacid generator is capable of producing a cured product free from corrosion of members and free from the problem that transparency is deteriorated by corrosion of a resin because a strong acid does not remain particularly after a heat resistance test; and a cured product.

Solutions to the Problems

The present inventors have found a sulfonium salt (an acid generator) suitable for the above-mentioned objects.

That is, the present invention provides a sulfonium salt formed of a sulfonium cation selected from a group indicated by general formulas (1), (2), and (3) and a gallate anion represented by formula (a); a photoacid generator that is characterized in that said sulfonium salt is contained therein; an energy-ray curable composition containing said photoacid generator and a cationic polymerizable compound; and a cured product formed by curing these substances.

[Chemical Formula 1]

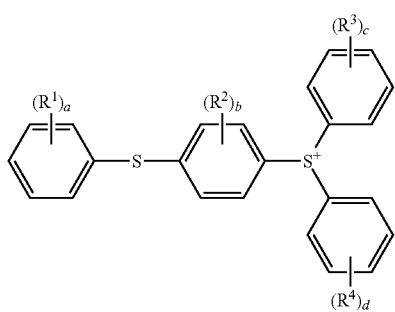

(1)

[in formula (1), $R^1$ to $R^4$ each independently represent an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an optionally substituted silyl group, an optionally substituted amino group, a cyano group, a nitro group, or a halogen atom; a, b, c, and d each represent the number of occurrences of each of $R^1$ to $R^4$; a represents an integer of 1 to 5; c and d represent an integer of 0 to 5; and b represents an integer of 0 to 4.]

[Chemical Formula 2]

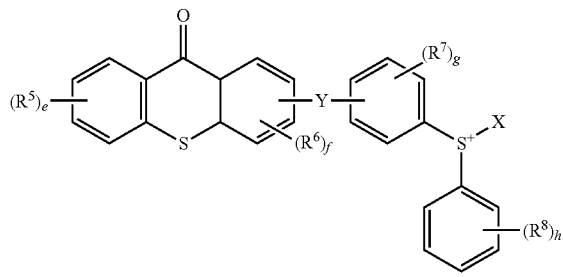

(2)

[in formula (2), $R^5$ to $R^8$ each independently represent an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an optionally substituted silyl group, an optionally substituted amino group, a cyano group, a nitro group, or a halogen atom; e, f, g, and h each represent the number of occurrences of each of $R^5$ to $R^8$; e and g represent an integer of 0 to 4; f represents an integer of 0 to 3; h represents an integer of 0 to 5; x represents an optionally substituted phenyl group or an optionally substituted thioxanthonyl group; Y represents —O—, —S—, —SO—, —SO$_2$— or —CO—.]

[Chemical Formula 3]

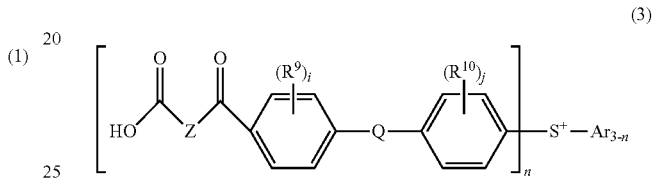

(3)

[in formula (3), n represents an integer of 1 to 3; $R^9$ to $R^{10}$ each independently represent an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an optionally substituted silyl group, an optionally substituted amino group, a cyano group, a nitro group, or a halogen atom; i and j each represent the number of occurrences of each of $R^9$ to $R^{10}$; i and j represent an integer of 0 to 4; Q represents single bond, —O— or —S—; Ar represents an aryl group having 6 to 14 carbon atoms (excluding the number of carbon atoms of substituents below), and some of hydrogen atoms in the aryl group may be substituted with an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an optionally substituted silyl group, an optionally substituted amino group, a cyano group, a nitro group, or a halogen atom; Z represents an alkylene group having 2 to 6 carbon atoms or a group represented by general formula (4) below; in formula (4), $R^{11}$ and $R^{12}$ represent a hydrogen atom, an alkyl group having 1 to 18 carbon atoms or an aryl group having 6 to 14 carbon atoms, and may be bonded to each other to form a ring structure.]

[Chemical Formula 4]

(4)

-continued

[Chemical Formula 5]

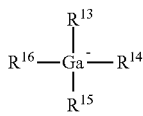

(a)

[in formula (a), $R^{13}$ to $R^{16}$ each independently represent a phenyl group or a perfluoroalkyl group, and some of hydrogen atoms in these groups may be substituted with a group selected from a perfluoroalkyl group, a perfluoroalkoxy group, a nitro group, a cyano group, an acyl group and a halogen atom.]

Effects of the Invention

A sulfonium salt and a photoacid generator containing the sulfonium salt of the present invention which does not contain a toxic metal, has cationic polymerization performance and crosslinking reaction performance equivalent to or higher than those of tetrakis(pentafluorophenyl)borate salt.

The cured product of an energy ray-curable composition containing the photoacid generator of the invention is free from the problem of corrosion of members and free from the problem that transparency is deteriorated by corrosion of a resin because a strong acid does not remain particularly after a heat resistance test.

MODE FOR CARRYING OUT THE INVENTION

Hereinafter, embodiments of the invention are described in detail.

A sulfonium salt of the present invention is formed of a sulfonium cation selected from a group indicated by general formulas (1), (2), and (3) and a gallate anion represented by formula (a).

In formula (1), examples of the alkyl group for $R^1$ to $R^4$ include straight chain alkyl groups having 1 to 18 carbon atoms (such as methyl, ethyl, n-propyl, n-butyl, n-pentyl, n-octyl, n-decyl, n-dodecyl, n-tetradecyl, n-hexadecyl, and n-octadecyl), branched chain alkyl groups having 3 to 18 carbon atoms (such as isopropyl, isobutyl, sec-butyl, tert-butyl, isopentyl, neopentyl, tert-pentyl, isohexyl, and isooctadecyl), and cycloalkyl groups having 3 to 18 carbon atoms (such as cyclopropyl, cyclobutyl, cyclopentyl, cyclohexyl, and 4-decylcyclohexyl).

In formula (1), examples of the alkoxy group for $R^1$ to $R^4$ include straight chain alkoxy groups having 1 to 18 carbon atoms or branched chain alkoxy groups having 3 to 18 carbon atoms (such as methoxy, ethoxy, propoxy, isopropoxy, butoxy, isobutoxy, sec-butoxy, tert-butoxy, hexyloxy, decyloxy, dodecyloxy, and octadecyloxy).

In formula (1), examples of the alkylcarbonyl group for $R^1$ to $R^4$ include straight alkylcarbonyl groups having 2 to 18 carbon atoms or branched chain alkylcarbonyl groups having 4 to 18 carbon atoms (such as acetyl, propionyl, butanoyl, 2-methylpropionyl, heptanoyl, 2-methylbutanoyl, 3-methylbutanoyl, octanoyl, decanoyl, dodecanoyl, and octadecanoyl).

In formula (1), examples of the arylcarbonyl group for $R^1$ to $R^4$ include arylcarbonyl groups having 7 to 11 carbon atoms (such as benzoyl and naphthoyl).

In formula (1), examples of the alkoxycarbonyl group for $R^1$ to $R^4$ include straight chain alkoxycarbonyl groups having 2 to 19 carbon atoms or branched chain alkoxycarbonyl groups having 4 to 19 carbon atoms (such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, octyloxycarbonyl, tetradecyloxycarbonyl, and octadecyloxycarbonyl).

In formula (1), examples of the aryloxycarbonyl group for $R^1$ to $R^4$ include aryloxycarbonyl groups having 7 to 11 carbon atoms (such as phenoxycarbonyl and naphthoxycarbonyl).

In formula (1), examples of the arylthiocarbonyl group for $R^1$ to $R^4$ include arylthiocarbonyl groups having 7 to 11 carbon atoms (such as phenylthiocarbonyl and naphthylthiocarbonyl).

In formula (1), examples of the acyloxy group for $R^1$ to $R^4$ include straight chain acyloxy groups having 2 to 19 carbon atoms or branched chain acyloxy groups having 4 to 19 carbon atoms (such as acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, octylcarbonyloxy, tetradecylcarbonyloxy, and octadecylcarbonyloxy).

In formula (1), examples of the arylthio group for $R^1$ to $R^4$ include arylthio groups having 6 to 20 carbon atoms (such as phenylthio, 2-methylphenylthio, 3-methylphenylthio, 4-methylphenylthio, 2-chlorophenylthio, 3-chlorophenylthio, 4-chlorophenylthio, 2-bromophenylthio, 3-bromophenylthio, 4-bromophenylthio, 2-fluorophenylthio, 3-fluorophenylthio, 4-fluorophenylthio, 2-hydroxyphenylthio, 4-hydroxyphenylthio, 2-methoxyphenylthio, 4-methoxyphenylthio, 1-naphthylthio, 2-naphthylthio, 4-[4-(phenylthio)benzoyl]phenylthio, 4-[4-(phenylthio)phenoxy]phenylthio, 4-[4-(phenylthio)phenyl]phenylthio, 4-(phenylthio)phenylthio, 4-benzoylphenylthio, 4-benzoyl-2-chlorophenylthio, 4-benzoyl-3-chlorophenylthio, 4-benzoyl-3-methylthiophenylthio, 4-benzoyl-2-methylthiophenylthio, 4-(4-methylthiobenzoyl)phenylthio, 4-(2-methylthiobenzoyl)phenylthio, 4-(p-methylbenzoyl)phenylthio, 4-(p-ethylbenzoyl)phenylthio, 4-(p-isopropylbenzoyl)phenylthio, and 4-(p-tert-butylbenzoyl)phenylthio).

In formula (1), examples of the alkylthio group for $R^1$ to $R^4$ include straight chain alkylthio groups having 1 to 18 carbon atoms or branched chain alkylthio groups having 3 to 18 carbon atoms (such as methylthio, ethylthio, propylthio, isopropylthio, butylthio, isobutylthio, sec-butylthio, tert-butylthio, pentylthio, isopentylthio, neopentylthio, tert-pentylthio, octylthio, decylthio, dodecylthio, and isooctadecylthio).

In formula (1), examples of the aryl group for $R^1$ to $R^4$ include aryl groups having 6 to 10 carbon atoms (such as phenyl, tolyl, dimethylphenyl, and naphthyl).

In formula (1), examples of the heterocyclic hydrocarbon group for $R^1$ to $R^4$ include heterocyclic hydrocarbon groups having 4 to 20 carbon atoms (such as thienyl, furanyl, pyranyl, pyrrolyl, oxazolyl, thiazolyl, pyridyl, pyrimidyl, pyrazinyl, indolyl, benzofuranyl, benzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl, and dibenzofuranyl).

In formula (1), examples of the aryloxy group for $R^1$ to $R^4$ include aryloxy groups having 6 to 10 carbon atoms (such as phenoxy and naphthyloxy).

In formula (1), examples of the alkylsulfinyl group for $R^1$ to $R^4$ include straight chain alkylsulfinyl groups having 1 to 18 carbon atoms or branched chain alkylsulfinyl groups having 3 to 18 carbon atoms (such as methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, isopentylsulfinyl, neopentylsulfinyl, tert-pentylsulfinyl, octylsulfinyl, and isooctadecylsulfinyl).

In formula (1), examples of the arylsulfinyl group for $R^1$ to $R^4$ include arylsulfinyl groups having 6 to 10 carbon atoms (such as phenylsulfinyl, tolylsulfinyl, and naphthylsulfinyl).

In formula (1), examples of the alkylsulfonyl group for $R^1$ to $R^4$ include straight chain alkylsulfonyl groups having 1 to 18 carbon atoms or branched chain alkylsulfonyl groups having 3 to 18 carbon atoms (such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, tert-pentylsulfonyl, octylsulfonyl, and octadecylsulfonyl).

In formula (1), examples of the arylsulfonyl group for $R^1$ to $R^4$ include arylsulfonyl groups having 6 to 10 carbon atoms (such as phenylsulfonyl, tolylsulfonyl (tosyl group), and naphthylsulfonyl).

In formula (1), examples of the hydroxy(poly)alkyleneoxy group for $R^1$ to $R^4$ include hydroxy(poly)alkyleneoxy groups represented by formula (5):

$$HO(-AO)_q- \quad (5)$$

[wherein AO represents an ethyleneoxy group and/or a propyleneoxy group, and q represents an integer of 1 to 5].

In formula (1), examples of the optionally substituted silyl group for $R^1$ to $R^4$ include an silyl group and substituted silyl groups having 1 to 2 carbon atoms (such as methylsilyl, dimethylsilyl, trimethylsilyl, phenylsilyl, methylphenylsilyl, dimethylphenyldilyl, diphenylsilyl, diphenylmethylsilyl, and triphenylsilyl.)

In formula (1), examples of the optionally substituted amino group for $R^1$ to $R^4$ include an amino group ($-NH_2$) and substituted amino groups having 1 to 15 carbon atoms (such as methylamino, dimethylamino, ethylamino, methylethylamino, diethylamino, n-propylamino, methyl-n-propylamino, ethyl-n-propylamino, n-propylamino, isopropylamino, isopropylmethylamino, isopropylethylamino, diisopropylamino, phenylamino, diphenylamino, methylphenylamino, ethylphenylamino, n-propylphenylamino, and isopropylphenylamino).

In formula (1), examples of the halogen atom for $R^1$ to $R^4$ include a fluorine atom, a chlorine atom, a bromine atom, and an iodine atom.

In formula (1), $R^1$ to $R^4$ are independent of one another and therefore may be the same as or different from one another.

$R^1$ to $R^4$ each preferably represent an alkyl group, an alkoxy group, an aryl group, an aryloxy group, an arylcarbonyl group, an alkylcarbonyl group, a silyl group, or a halogen atom, and in particular, preferably represent a methyl group, a methoxy group, a phenyl group, a phenoxy group, a phenylcarbonyl group, an acetyl group, a trimethyl silyl group, a chlorine atom, and a bromine atom.

$R^1$ to $R^4$ is more preferably a group selected from an alkylcarbonyl group, an aryl group, a silyl group, an arylcarbonyl group, an aryloxy group, and in particular, preferably an aryl group, and an alkylcarbonyl group.

In formula (1), a, b, c, and d each represent the number of occurrences of each of $R^1$ to $R^4$, a represents an integer of 1 to 5, preferably 1 to 3, more preferably 1 to 2, in particular, preferably 1; c and d represent an integer of 0 to 5, preferably 0 to 3, more preferably 0 to 2, in particular, preferably 0; b represents an integer of 0 to 4, preferably 0 to 3, more preferably 0 to 2, in particular, preferably 0. When a, b, c, and d are each in the preferred range, the sulfonium salt will have higher photosensitivity.

Preferred specific examples of the sulfonium cation represented by formula (1) are shown below.

[Chemical Formula 6]

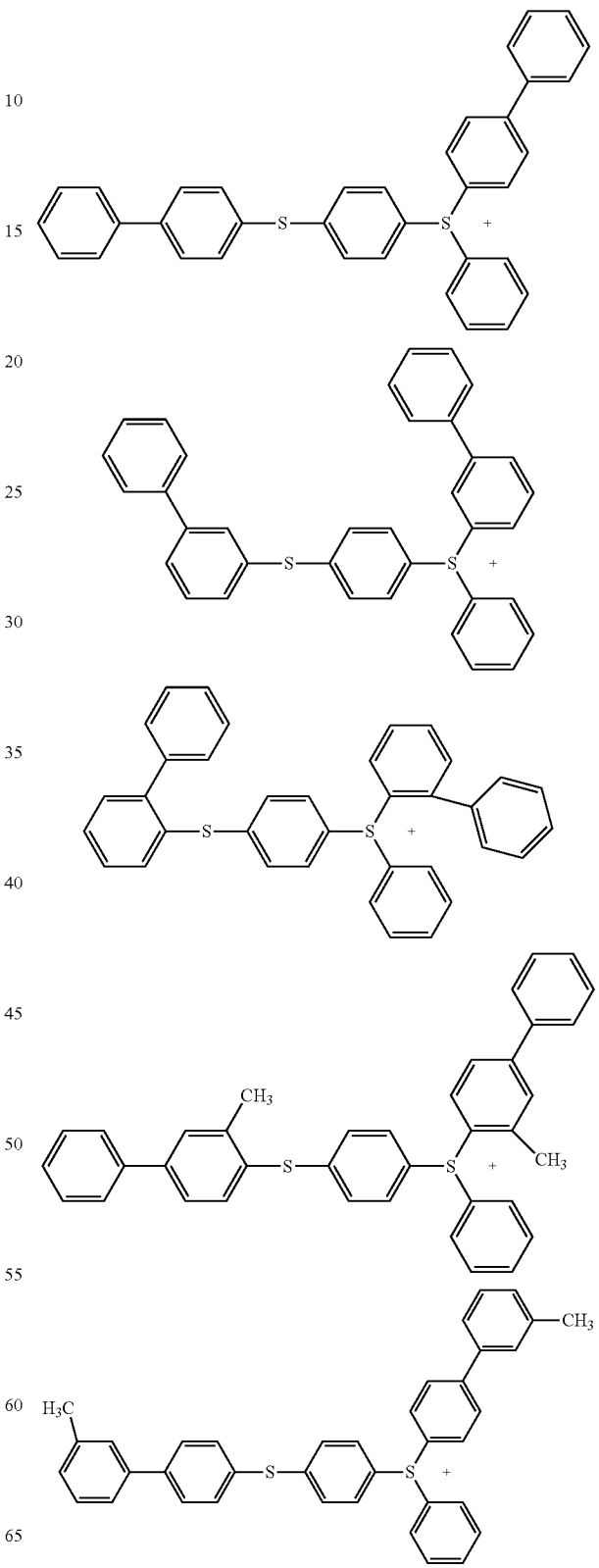

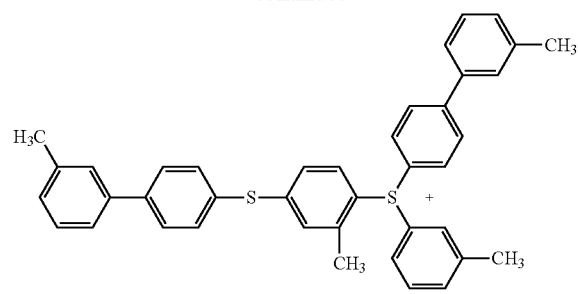
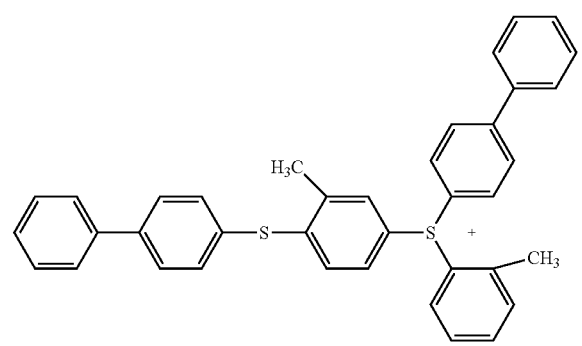
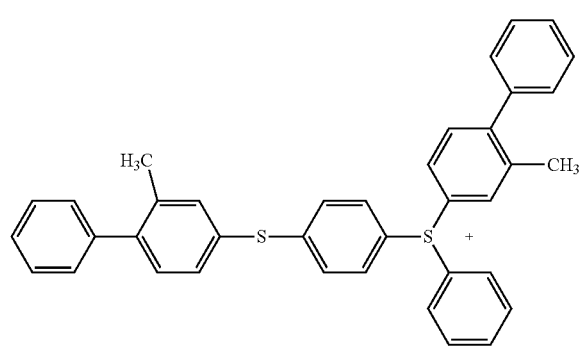
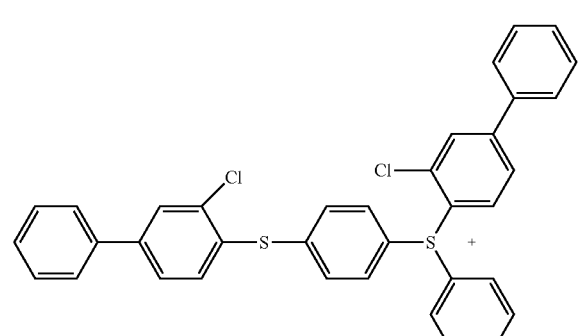
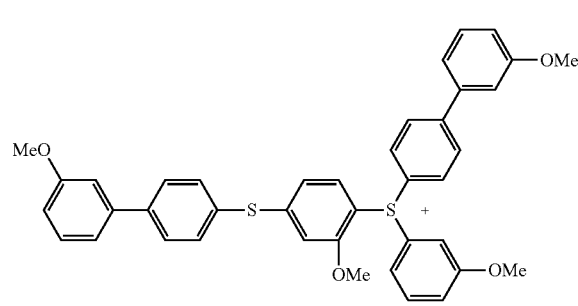
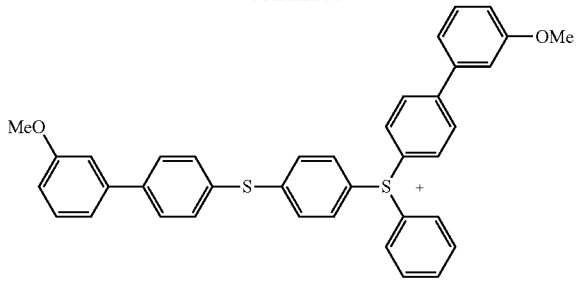
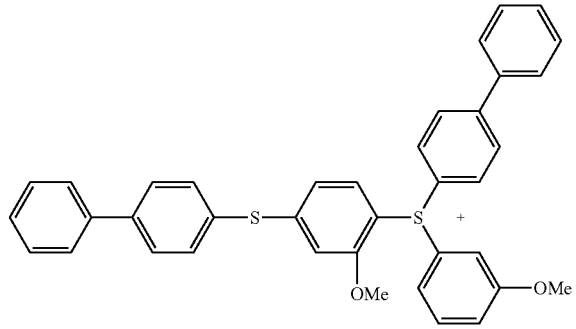
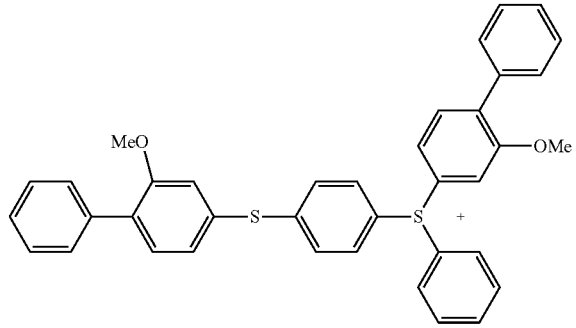
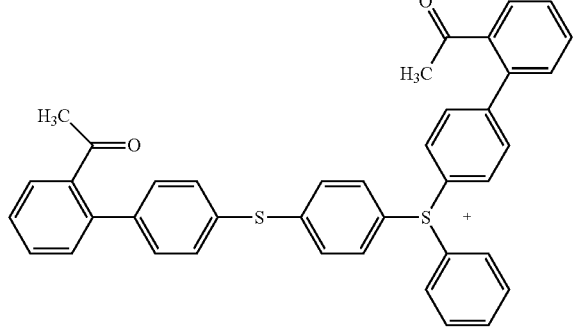
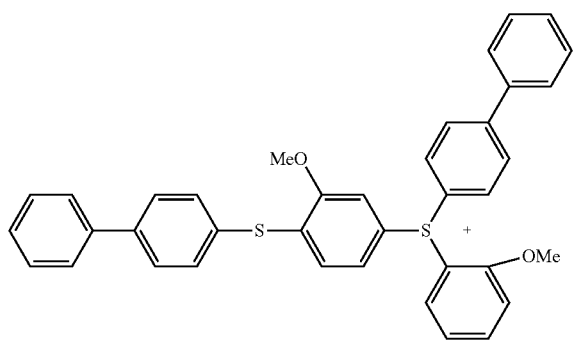

[Chemical Formula 7]
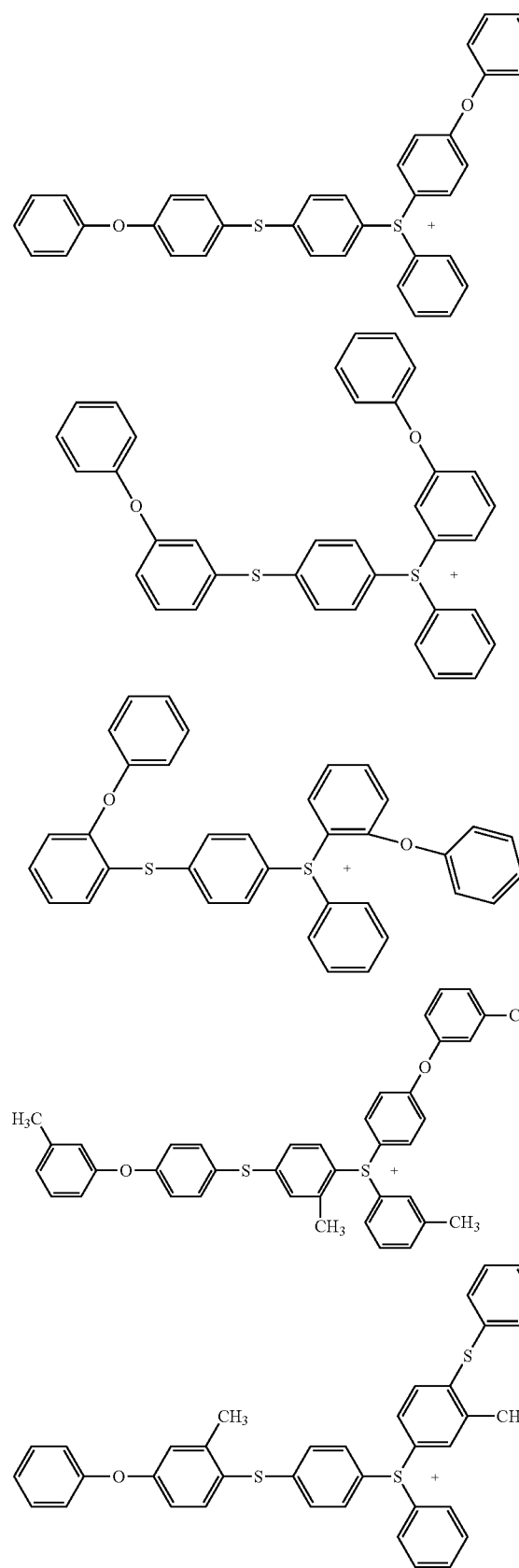
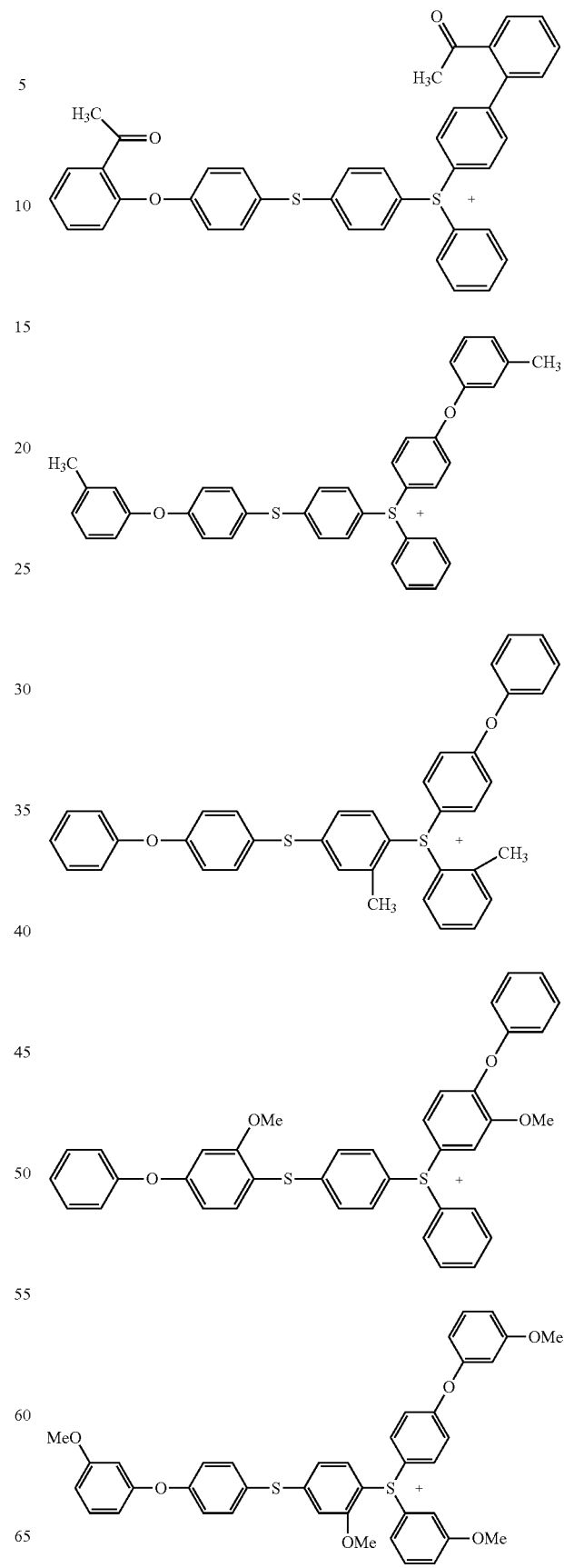

-continued
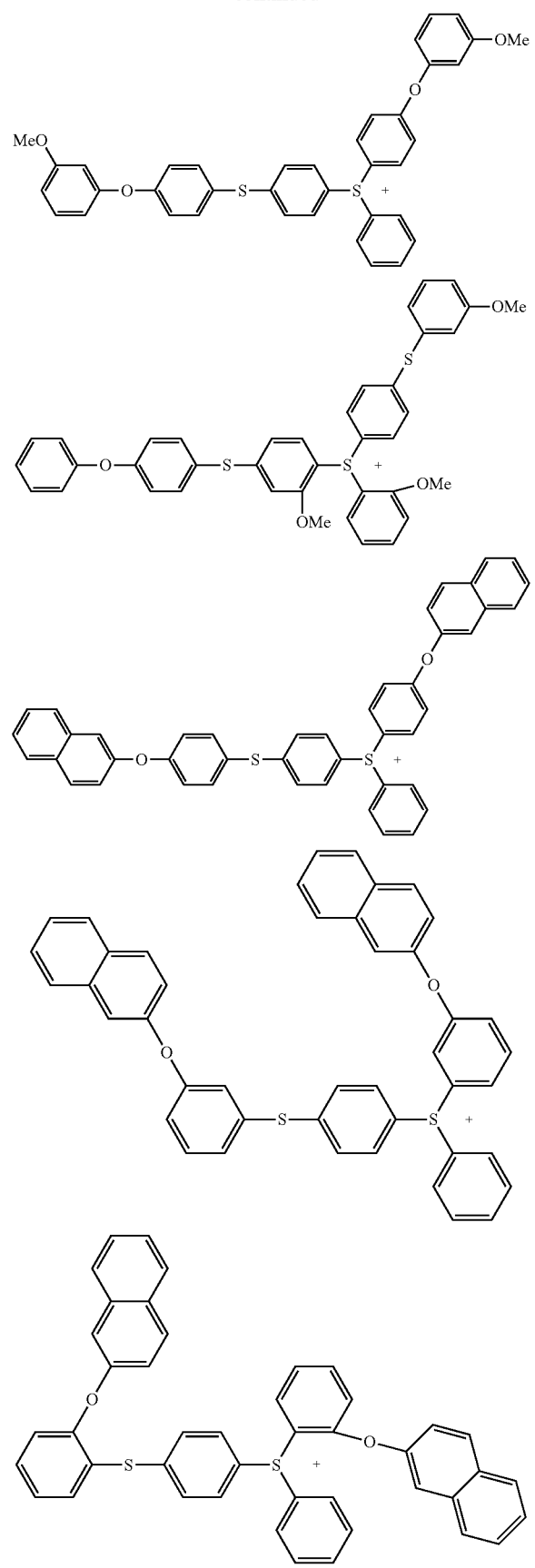
[Chemical Formula 8]
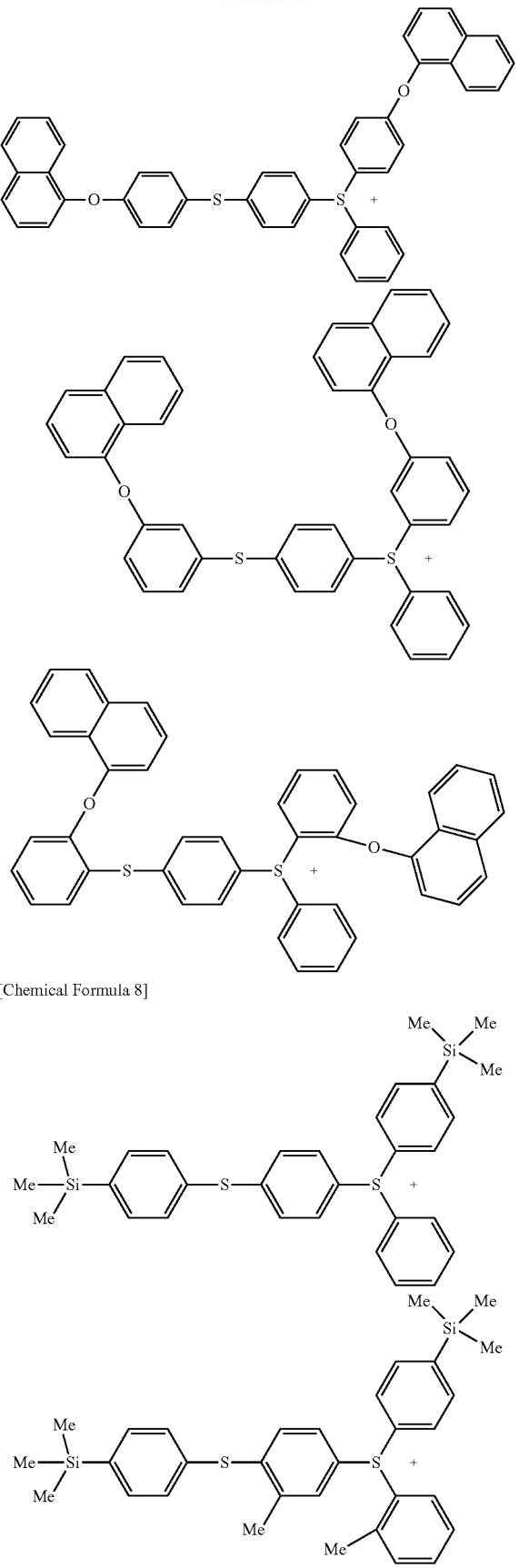

-continued
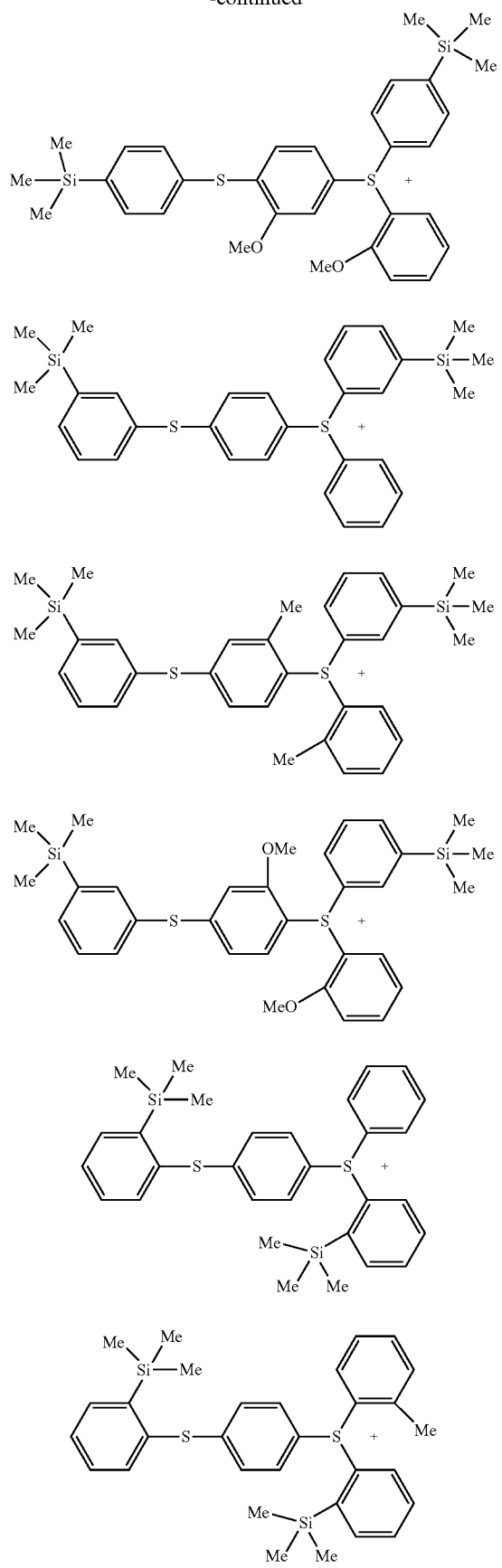
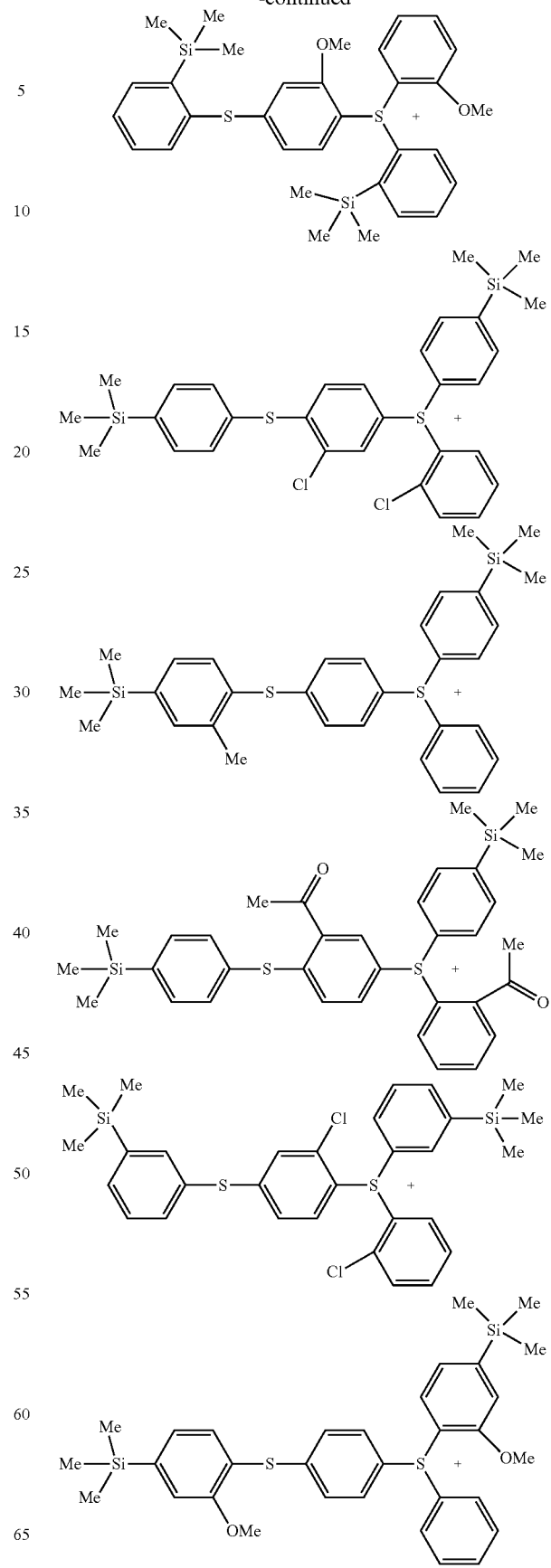

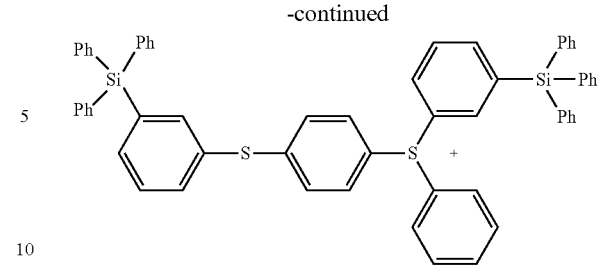
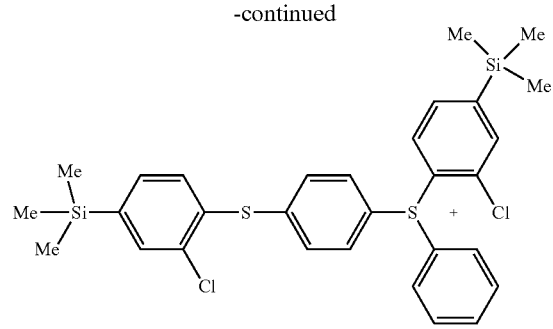
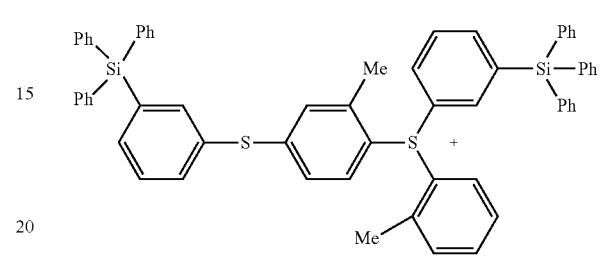
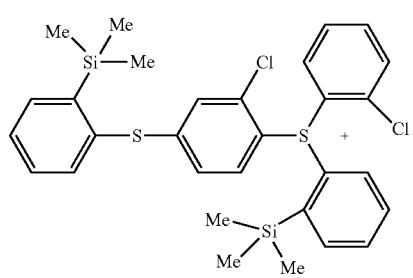
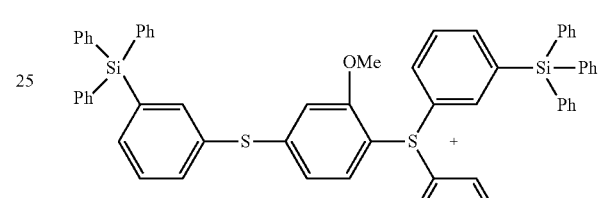
[Chemical Formula 9]
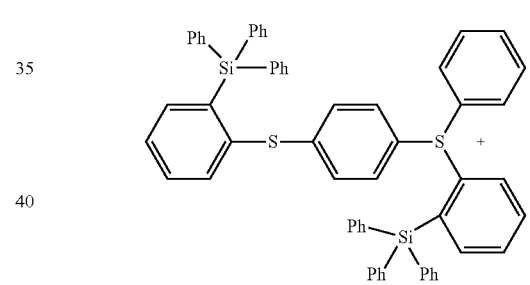
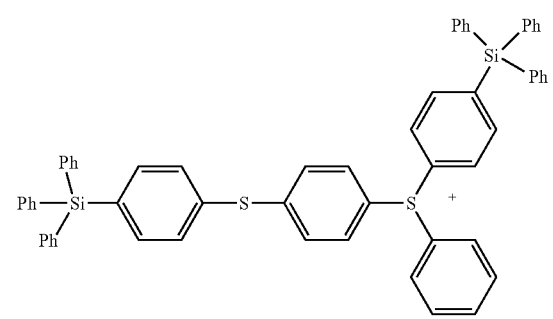
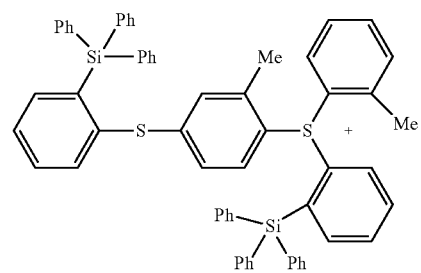
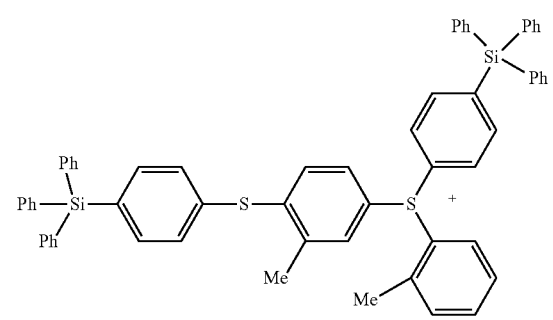
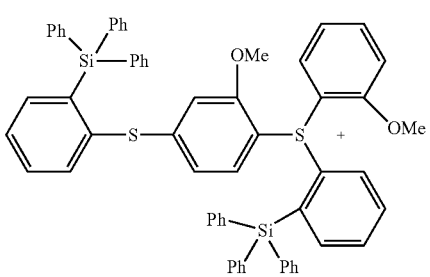
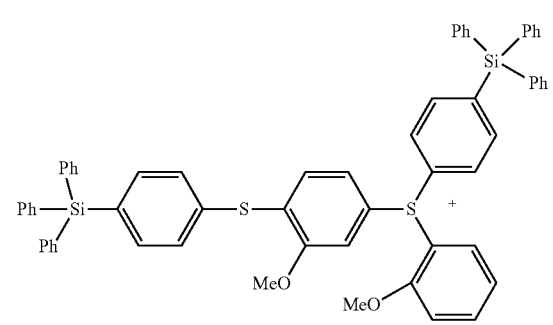

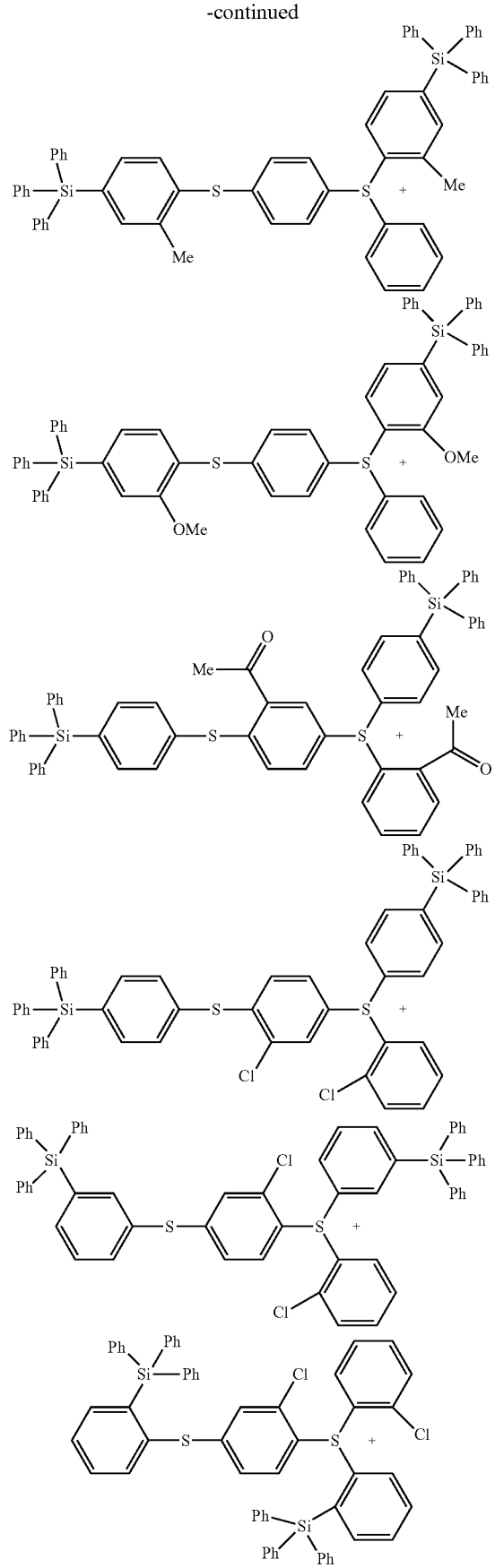
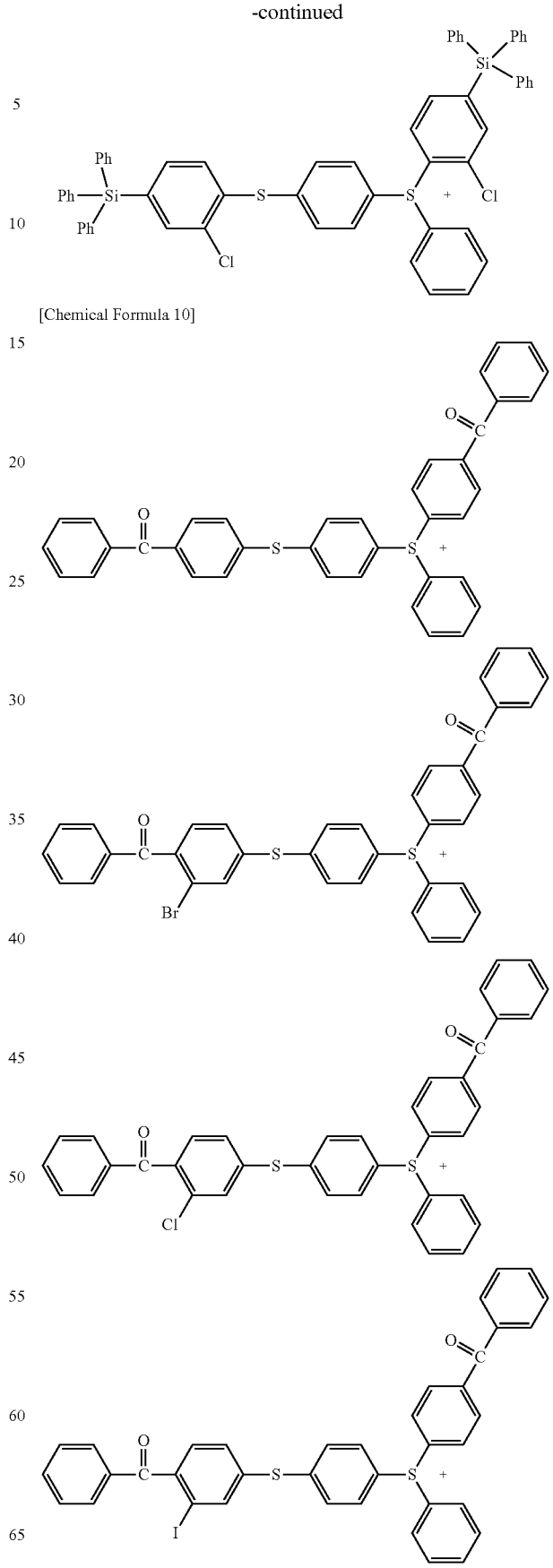
[Chemical Formula 10]

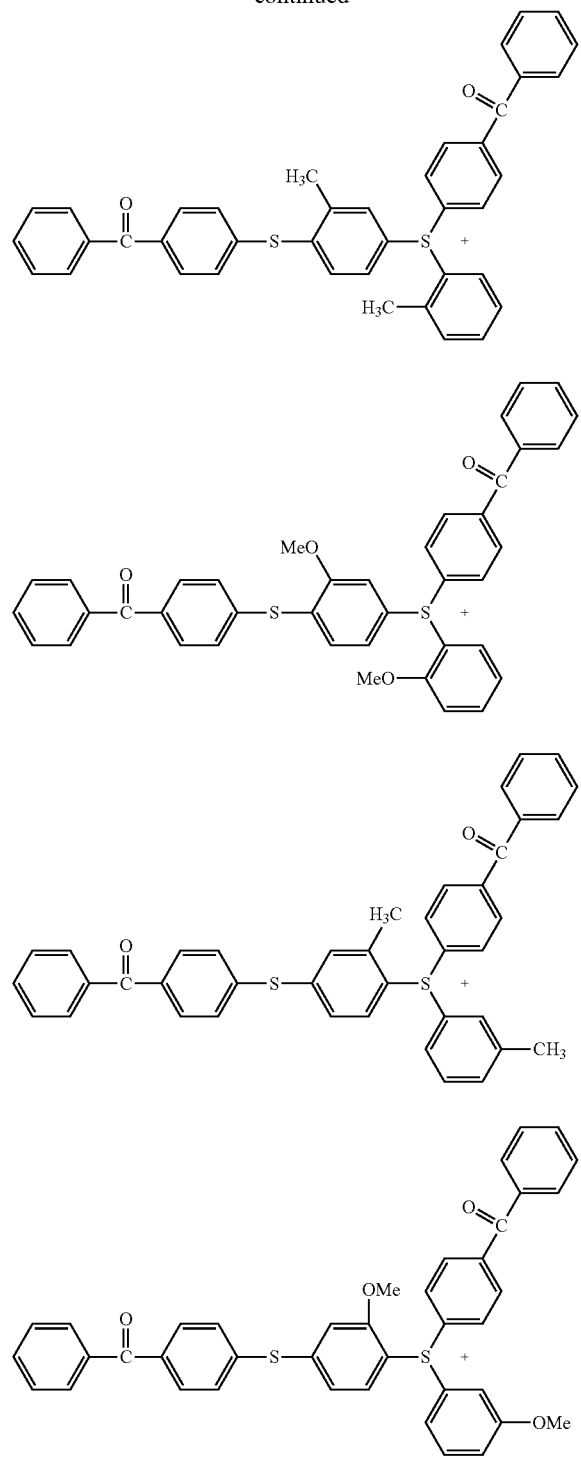

[Chemical Formula 11]

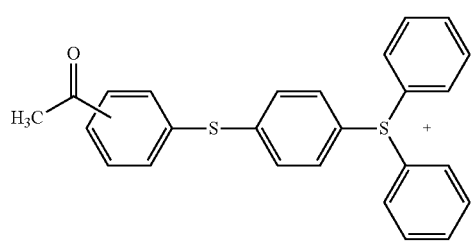

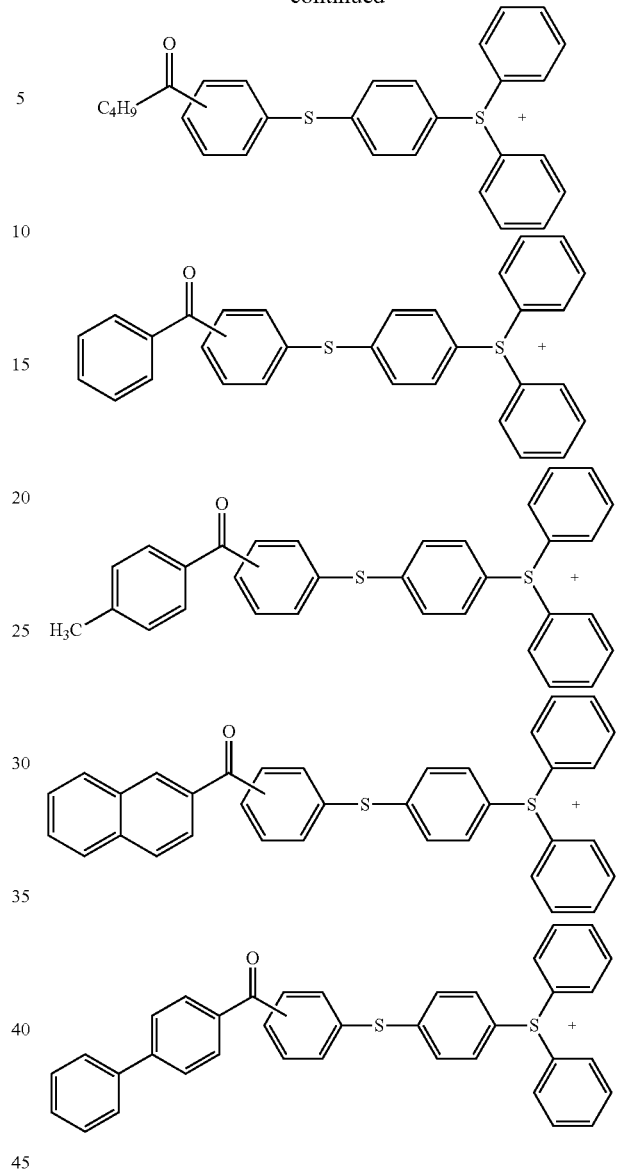

In formula (2), as $R^5$ to $R^8$, examples of the alkyl group, the hydroxy group, the alkoxy group, the alkylcarbonyl group, the arylcarbonyl group, the alkoxycarbonyl group, the aryloxycarbonyl group, the arylthiocarbonyl group, the acyloxy group, the arylthio group, the alkylthio group, the aryl group, the heterocyclic hydrocarbon group, the aryloxy group, the alkylsulfinyl group, the arylsulfinyl group, the alkylsulfonyl group, the arylsulfonyl group, the hydroxy (poly)alkyleneoxy group, the optionally substituted silyl group, the optionally substituted amino group, the cyano group, the nitro group, or the halogen atom are the same as those listed as $R^1$ to $R^4$ for formula (1).

In formula (2), $R^5$ to $R^8$ are independent of one another and therefore may be the same as or different from one another.

$R^5$ to $R^8$ each preferably represent an alkyl group, an alkoxy group, an aryl group, an aryloxy group, an arylcarbonyl group, an alkylcarbonyl group, a silyl group, or a halogen atom, and in particular, preferably represent a methyl group, a methoxy group, a phenyl group, a phenoxy group, a phenylcarbonyl group, an acetyl group, a trimethyl silyl group, a chlorine atom, and a bromine atom.

In formula (2), e, f, g, and h each represent the number of occurrences of each of $R^5$ to $R^8$, a represents an integer of 0 to 4, preferably 0 to 3, more preferably 0 to 2, in particular, preferably 0; f represents an integer of 0 to 3, preferably 0 to 2, in particular, preferably 0; h represents an integer of 0 to 5, preferably 0 to 3, more preferably 0 to 2, in particular, preferably 0. When e, f, g, and h are each in the preferred range, the sulfonium salt will have higher photosensitivity.

In formula (2), examples of the optionally substituted phenyl group for X include a tolyl and a dimethylphenyl.

In formula (2), examples of the optionally substituted thioxanthonyl group for X include a 7-isopropylthioxanthonyl and 7-chlorothioxanthonyl.

X preferably represents an optionally substituted thioxanthonyl group.

In formula (2), Y represents —O—, —S—, —SO—, —SO$_2$— or —CO—, and preferably —S—.

Preferred specific examples of the sulfonium cation represented by formula (2) are shown below.

[Chemical Formula 12]

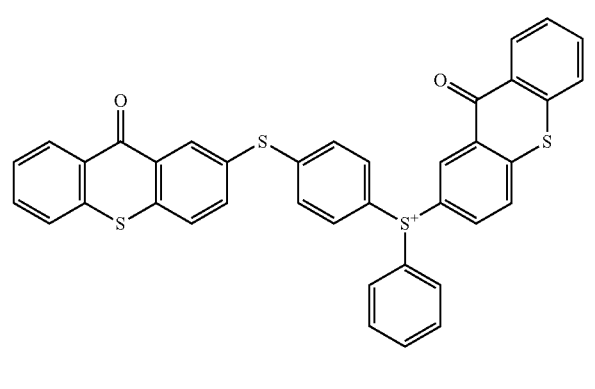

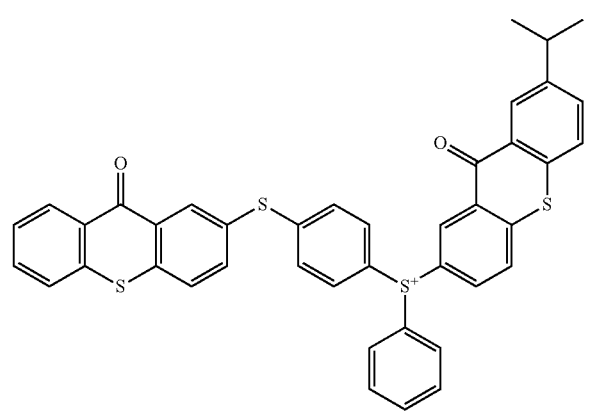

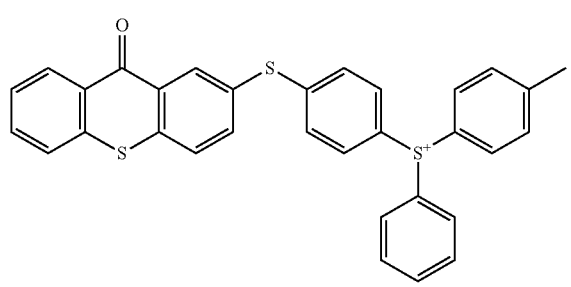

-continued

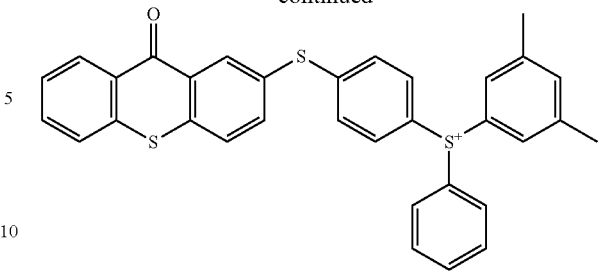

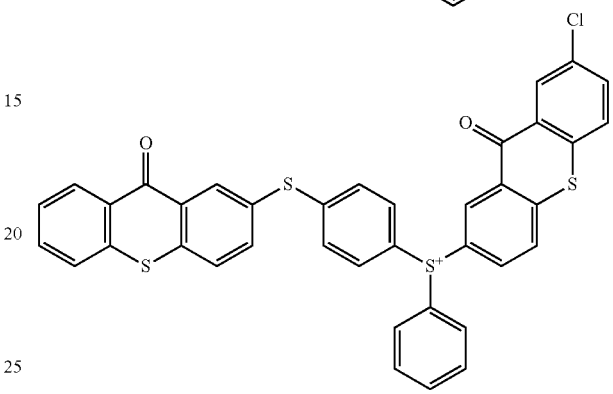

In formula (3), as $R^9$ to $R^{10}$, examples of the alkyl group, the hydroxy group, the alkoxy group, the alkylcarbonyl group, the arylcarbonyl group, the alkoxycarbonyl group, the aryloxycarbonyl group, the arylthiocarbonyl group, the acyloxy group, the arylthio group, the alkylthio group, the aryl group, the heterocyclic hydrocarbon group, the aryloxy group, the alkylsulfinyl group, the arylsulfinyl group, the alkylsulfonyl group, the arylsulfonyl group, the hydroxy (poly)alkyleneoxy group, the optionally substituted silyl group, the optionally substituted amino group, or the halogen atom are the same as those listed as $R^1$ to $R^4$ for formula (1).

In formula (3), examples of the aryl group having 6 to 14 carbon atoms (excluding the number of carbon atoms of substituents below) for Ar include monocyclic aryl groups (such as a phenyl), fused polycyclic aryl groups (such as naphthyl, anthracenyl, phenanthrenyl, anthraquinolyl, fluorenyl and naphthoquinolyl), and aromatic heterocyclic hydrocarbon groups (such as monocyclic heterocyclic rings such as thienyl, furanyl, pyranyl, pyrrolyl, oxazolyl, thiazolyl, pyridyl, pyrimidyl and pyrazinyl; and fused polycyclic heterocyclic rings such as indolyl, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, coumarinyl, dibenzothienyl, xanthonyl, thioxanthonyl and dibenzofuranyl).

Ar represents an aryl group having 6 to 14 carbon atoms (excluding the number of carbon atoms of substituents below), and some of hydrogen atoms in the aryl group may be substituted with an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an optionally substituted silyl group, an optionally substituted amino group, a cyano group, a nitro group, or a halogen atom. These substituents are the same as are the same as those listed as $R^1$ to $R^4$ for formula (1).

In formula (3), $R^9$ to $R^{10}$ are independent of one another and therefore may be the same as or different from one another.

In formula (3), $R^9$ to $R^{10}$ preferably represent an alkyl group, an alkoxy group, an aryl group, an aryloxy group, an arylcarbonyl group, an alkylcarbonyl group, a silyl group, or a halogen atom, and in particular, preferably represent a methyl group, a methoxy group, a phenyl group, a phenoxy group, a phenylcarbonyl group, an acetyl group, a trimethyl silyl group, a chlorine atom, and a bromine atom.

In formula (3), i and j each represent the number of occurrences of each of $R^9$ to $R^{10}$, i and j represent an integer of 0 to 4, preferably 0 to 3, more preferably 0 to 2, in particular, preferably 0. When i and j are each in the preferred range, the sulfonium salt will have higher photosensitivity.

In formula (3), Ar represents preferably phenyl group; n represents an integer of 1 to 3, and preferably 1; Q represents single bond, —O— or —S—, and preferably —S—.

In formula (3), Z represents an alkylene group having 2 to 6 carbon atoms or a group represented by general formula (4) above; examples of the alkylene group having 2 to 6 carbon atoms for Z include an ethylene group, a propylene group, and a butylenes group.

In formula (4), as $R^{11}$ to $R^{12}$, examples of the alkyl group having 1 to 18 carbon atoms and aryl group having 6 to 14 carbon atoms are the same as those listed above.

Specific examples of the sulfonium cation represented by formula (3) are shown below.

[Chemical Formula 13]

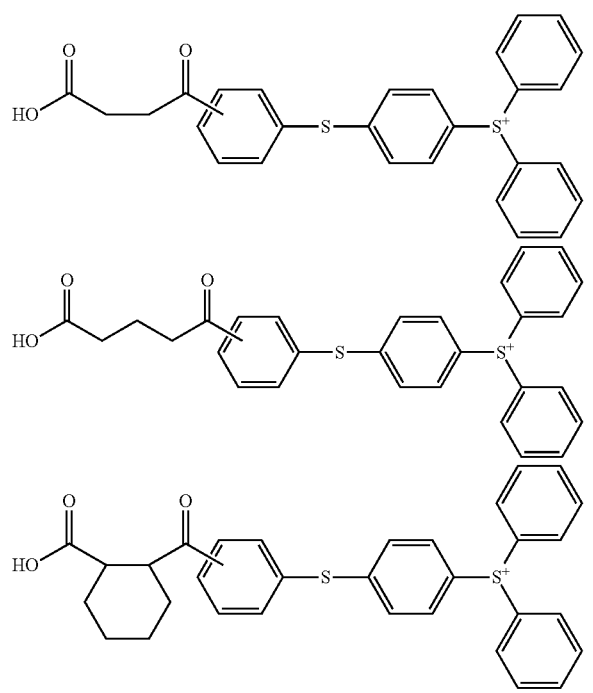

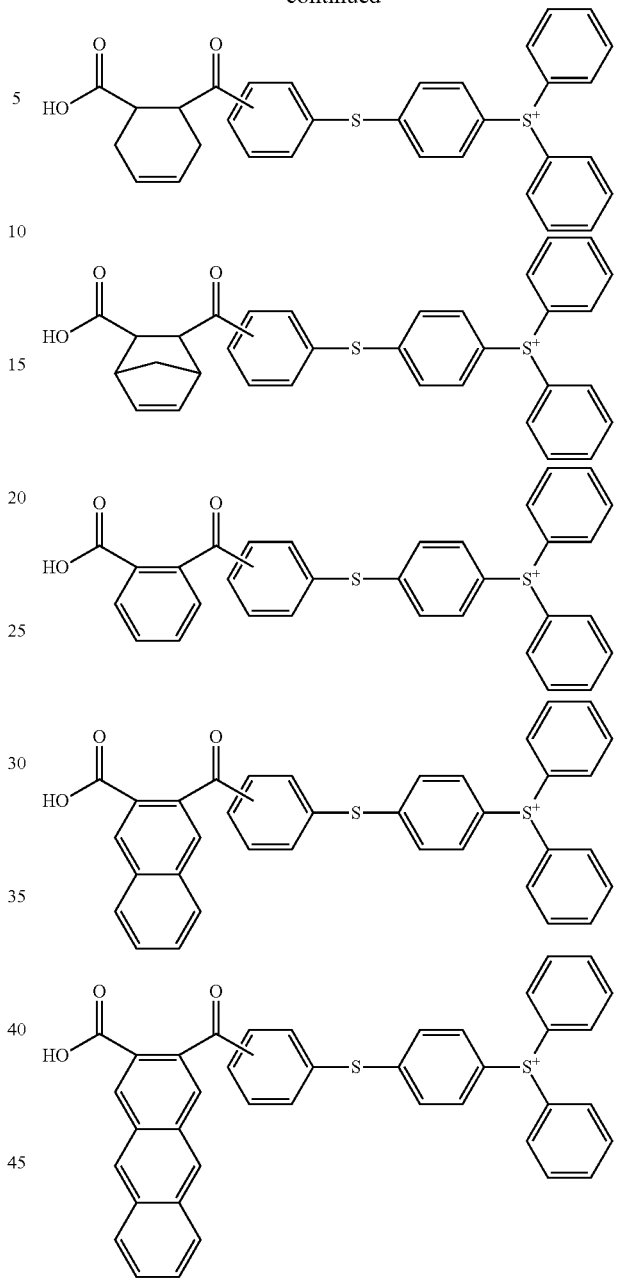

In a gallate anion represented by formula (a), $R^{13}$ to $R^{16}$ each independently represent a phenyl group or a perfluoroalkyl group, and some of hydrogen atoms in these groups may be substituted with a group selected from a perfluoroalkyl group, a perfluoroalkoxy group, a nitro group, a cyano group, an acyl group and a halogen atom.

The perfluoroalkyl group has 1 to 8 carbon atoms, and preferably 1 to 4 carbon atoms. Examples of the perfluoroalkyl group include straight chain perfluoroalkyl group such as trifluoromethyl, pentafluoroethyl, heptafluoropropyl, nonafluorobutyl, perfluoropentyl, perfluorooctyl; branched chain perfluoroalkyl group such as heptafluoro-iso-propyl, nonafluoro-iso-butyl, nonafluoro-sec-butyl, nonafluoro-tert-butyl; in addition, other perfluoroalkyl group such as perfluorocyclopropyl, perfluorocyclobuthyl, perfluorocyclopenthyl, perfluorocyclohexyl.

The perfluoroalkoxy group has 1 to 8 carbon atoms, and preferably 1 to 4 carbon atoms. Examples of the perfluoroalkoxy group include straight chain perfluoroalkoxy group such as trifluoromethoxy, pentafluoroethoxy, heptafluoropropoxy, nonafluorobutoxy, perfluoropentyloxy, perfluorooctyloxy; branched chain perfluoroalkoxy group such as heptafluoro-iso-propoxy, nonafluoro-iso-butoxy, nonafluoro-sec-butoxy, nonafluoro-tert-butoxy.

Examples of the halogen atom include a fluorine atom, a chlorine atom, a bromine atom, and an iodine atom.

Examples of the perfluoroalkyl group are the same as those listed above.

From the viewpoint of cationic polymerization performance, $R^{13}$ to $R^{16}$ is preferably a phenyl group substituted with at least one selected from the group of a perfluoroalkyl group and a fluorine atom.

Preferable examples of $R^{13}$ to $R^{16}$ include pentafluorophenyl group ($C_6F_5$), trifluorophenyl group ($C_6H_2F_3$), tetrafluorophenyl group ($C_6HF_4$), trifluoromethylphenyl group ($CF_3C_6H_4$), bis(trifluoromethyl)phenyl group (($CF_3)_2C_6H_3$) pentafluoroethylphenyl group ($CF_3CF_2C_6H_4$), bis(pentafluoroethyl)phenyl group (($CF_3CF_2)_2C_6H_3$), fluoro-trifluoromethylphenyl group ($CF_3C_6H_3F$), fluoro-bis(trifluoromethyl)phenyl group (($CF_3)_2C_6H_2F$), fluoropentafluoroethylphenyl group ($CF_3CF_2C_6H_3F$), fluoro-bis(pentafluoroethyl)phenyl group (($CF_3CF_2)_2C_6H_2F$), pentaclorophenyl group ($C_6CL_5$), trichlorophenyl group ($C_6H_2CL_3$), tetraclorophenyl group ($C_6HCL_4$), triclorometylphenyl group ($CCL_3C_6H_4$), bis(trichloromethyl)phenyl group (($CCL_3)_2C_6H_3$), pentacloroethylphenyl group ($CCL_3CCL_2C_6H_4$), bis(pentacloroethyl)phenyl group (($CCL_3CCL_2)_2C_6H_3$), cloro-tricloromethylphenyl group ($CCL_3C_6H_3CL$), cloro-bis(triclorometyl)phenyl group (($CCL_3)_2C_6H_2CL$), cloro-pentacloroethylphenyl group ($CCL_3CCL_2C_6H_3CL$), cloro-bis(pentacloroethylphenyl group (($CCL_3CCL_2)_2C_6H_2CL$), nitrophenyl group ($C_6H_4NO_2$), cyano phenyl group ($NCC_6H_4$), acylphenyl group ($CH_3COC_6H_4$).

Among them, more preferred are pentafluorophenyl group ($C_6F_5$), and bis(trifluoromethyl)phenyl group (($CF_3)_3C_6H_3$), and in particular, preferred is pentafluorophenyl group ($C_6F_5$).

Specific examples of the gallate anion represented by formula (a) are shown below.

[Chemical Formula 14]

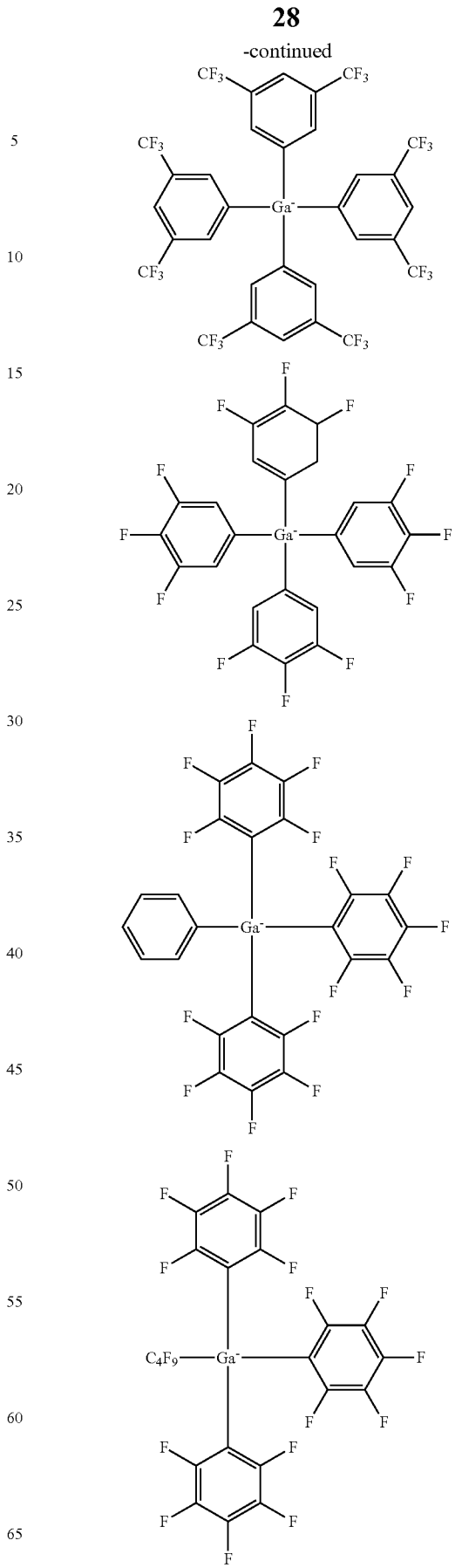

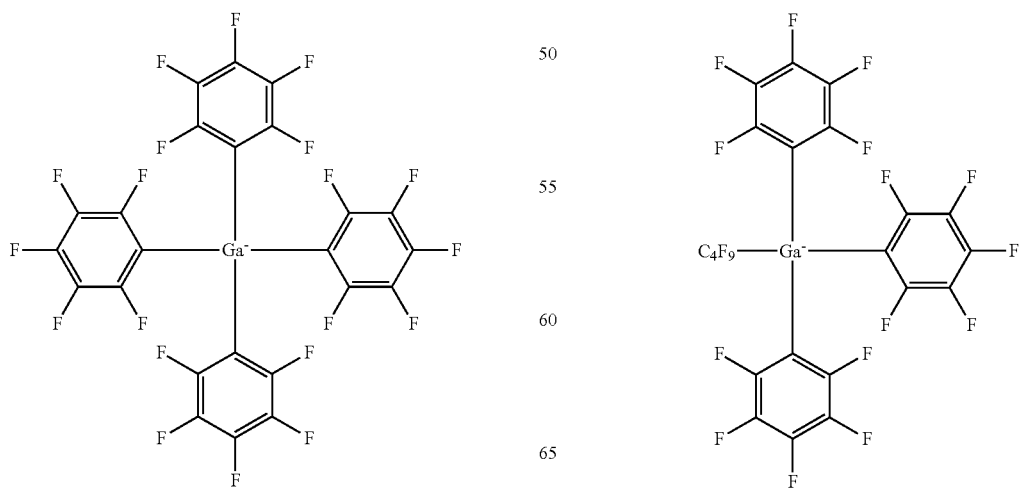

-continued

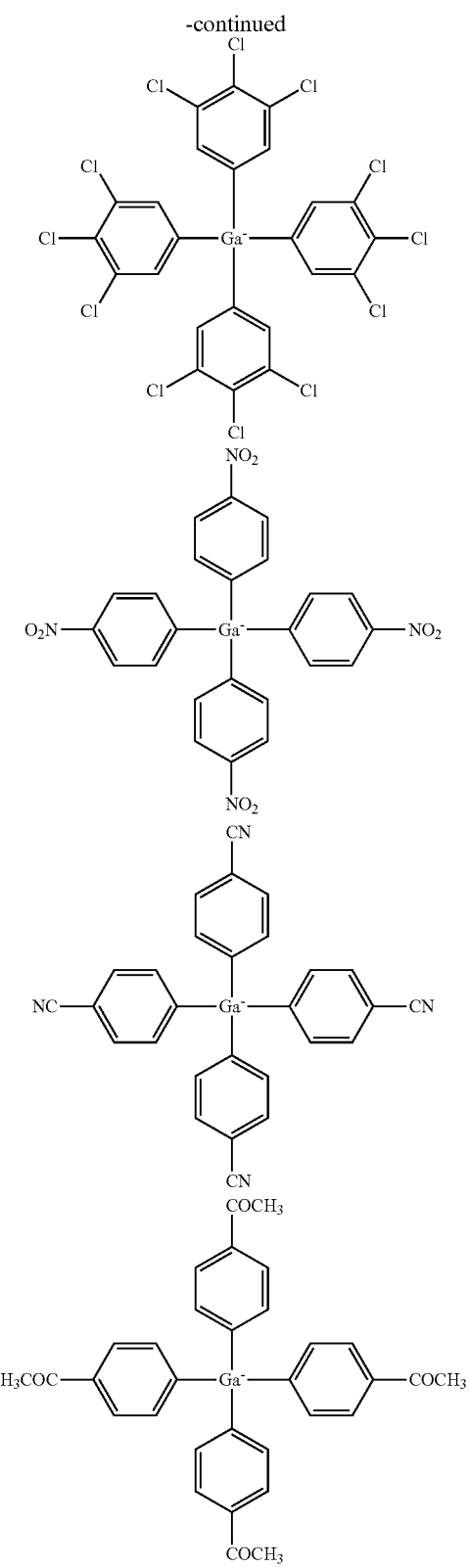

For ensuring that the sulfonium salt formed of a sulfonium cation selected from a group indicated by general formulas (1), (2), and (3) and a gallate anion represented by formula (a) (photoacid generator) is easily dissolved in a cationic polymerizable compound, the sulfonium salt may be previously dissolved in a solvent which does not hinder polymerization or crosslinking reaction.

Examples of the solvent include carbonates such as propylene carbonate, ethylene carbonate, 1,2-butylene carbonate, dimethyl carbonate, and diethyl carbonate; ketones such as acetone, methyl ethyl ketone, cyclohexanone, methyl isoamyl ketone, and 2-heptanone; polyhydric alcohols and derivatives thereof, such as monomethyl ethers, monoethyl ethers, monopropyl ethers, monobutyl ethers, or monophenyl ethers of ethylene glycol, ethylene glycol monoacetate, diethylene glycol, diethylene glycol monoacetate, propylene glycol, propylene glycol monoacetate, dipropylene glycol, and dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, ethyl pyruvate, ethyl ethoxyacetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanoate, 3-methoxybutyl acetate, and 3-methyl-3-methoxybutyl acetate; and aromatic hydrocarbons such as toluene and xylene.

When a solvent is used, the amount of the solvent used is preferably from 15 to 1000 parts by weight, more preferably from 30 to 500 parts by weight, based on 100 parts by weight of the sulfonium salt formed of a sulfonium cation selected from a group indicated by general formulas (1), (2), and (3) and a gallate anion represented by formula (a) (photoacid generator) in the present invention. A single solvent may be used alone or two or more solvents may be used in combination.

The energy ray-curable composition in the present invention (hereinafter, referred to as a curable composition) contains the above-mentioned photoacid generator and a cationic polymerizable compound.

Examples of the cationic polymerizable compound as a constituent component of the curable composition include cyclic ethers (such as epoxide and oxetane), ethylenically unsaturated compounds (such as vinyl ether and styrene species), bicycloorthoesters, spiroorthocarbonates, and spiroorthoesters Known epoxides and the like may be used as epoxides, examples of which include aromatic epoxides, alicyclic epoxides, and aliphatic epoxides.

Examples of the aromatic epoxides include glycidyl ethers of monohydric or polyhydric phenols having at least one aromatic ring (such as phenol, bisphenol A, phenol novolac, and alkylene oxide adducts thereof).

Examples of the alicyclic epoxides include compounds obtained by epoxidation of compounds having at least one cyclohexene or cyclopentene ring with an oxidizing agent (such as 3,4-epoxycyclohexylmethyl-3,4-epoxycyclohexanecarboxylate).

Examples of the aliphatic epoxides include polyglycidyl ethers of aliphatic polyhydric alcohols or alkylene oxide adducts thereof (such as 1,4-butanediol diglycidyl ether and 1,6-hexanediol diglycidyl ether), polyglycidyl esters of aliphatic polybasic acids (such as diglycidyl tetrahydrophthalate), and epoxidized long-chain unsaturated compounds (such as epoxidized soybean oil and epoxidized polybutadiene).

Known oxetanes and the like may be used as oxetanes, examples of which include 3-ethyl-3-hydroxymethyloxetane, 2-ethylhexyl(3-ethyl-3-oxetanylmethyl)ether, 2-hydroxyethyl(3-ethyl-3-oxetanylmethyl)ether, 2-hydroxypropyl(3-ethyl-3-oxetanylmethyl)ether, 1,4-bis[(3-ethyl-3- oxetanylmethoxy)methyl]benzene, oxetanylsilsesquioxetane, and phenol novolac oxetane.

Known cationic polymerizable monomers and the like may be used as ethylenically unsaturated compounds, examples of which include aliphatic monovinyl ethers, aromatic monovinyl ethers, polyfunctional vinyl ethers, styrenes, and cationic polymerizable nitrogen-containing monomers.

Examples of the aliphatic monovinyl ethers include methyl vinyl ether, ethyl vinyl ether, butyl vinyl ether, and cyclohexyl vinyl ether.

Examples of the aromatic monovinyl ethers include 2-phenoxyethyl vinyl ether, phenyl vinyl ether, and p-methoxyphenyl vinyl ether.

Examples of the polyfunctional vinyl ethers include butanediol-1,4-divinyl ether and triethylene glycol divinyl ether.

Examples of the styrene species include styrene, α-methylstyrene, p-methoxystyrene, and p-tert-butoxystyrene.

Examples of the cationic polymerizable nitrogen-containing monomers include N-vinylcarbazole and N-vinylpyrrolidone.

Examples of the bicycloorthoesters include 1-phenyl-4-ethyl-2,6,7-trioxabicyclo[2.2.2]octane and 1-ethyl-4-hydroxymethyl-2,6,7-trioxabicyclo[2.2.2]octane.

Examples of the spiroorthocarbonates include 1,5,7,11-tetraoxaspiro[5.5]undecane and 3,9-dibenzyl-1,5,7,11-tetraoxaspiro[5.5]undecane.

Examples of the spiroorthoesters include 1,4,6-trioxaspiro[4.4]nonane, 2-methyl-1,4,6-trioxaspiro[4.4]nonane, and 1,4,6-trioxaspiro[4.5]decane.

Further, a polyorganosiloxane having at least one cationic polymerizable group in one molecule can be used (those described in JP-A No. 2001-348482, JP-A No. 2000-281965, JP-A No. 7-242828, JP-A No. 2008-195931, Journal of Polym. Sci., Part A, Polym. Chem., Vol. 28, 497 (1990) and so on).

These polyorganosiloxanes may be any one of straight chain, branched chain and cyclic polyorganosiloxanes, or a mixture thereof.

Among these cationic polymerizable compounds, epoxides, oxetanes, and vinyl ethers are preferred, epoxides and oxetane are more preferred, and alicyclic epoxides and oxetanes are particularly preferred. These cationic polymerizable compounds may be used alone or in combination of two or more.

The content of the sulfonium salt formed of a sulfonium cation selected from a group indicated by general formulas (1), (2), and (3) and a gallate anion represented by formula (a) (photoacid generator) of the invention in a curable composition is preferably from 0.05 to 20 parts by weight, more preferably from 0.1 to 10 parts by weight, based on 100 parts by weight of the cationic polymerizable compound. Within the range, the cationic polymerizable compound can be more sufficiently polymerized, so that the physical properties of the cured product can be further improved. It will be understood that the content may be determined taking into account various factors such as the properties of the cationic polymerizable compound, the type and irradiation dose of the active energy ray, the temperature, the curing time, the humidity, and the thickness of the coating film, and is not limited to the above range.

If necessary, the curable composition of the invention may contain known additives (such as a sensitizer, a pigment, a filler, an electroconductive particle, an antistatic agent, a flame retardant, an anti-foaming agent, a fluidity controlling agent, a light stabilizer, an antioxidant, a tackifier, an ion scavenger, an anti-coloring agent, a solvent, a nonreactive resin, and a radically-polymerizable compound).

Basically, a sensitizer does not need to be contained in the curable composition of the present invention, but a sensitizer as an agent that complements the curability can be contained therein, as necessary. As such a sensitizer, a known (JP-A-11-279212, JP-A-09-183960, or the like) sensitizer and the like can be used, and examples thereof include anthracenes {anthracene, 9,10-dibutoxyanthracene, 9,10-dimethoxyanthracene, 2-ethyl-9,10-dimethoxyanthracene, 2-tert-buthyl-9,10-dimethoxyanthracene, 2,3-dimethyl-9,10-dimethoxyanthracene, 9-methoxy-10-methylanthracene, 9,10-diethoxyanthracene, 2-ethyl-9,10-dimethoxyanthracene, 2-tert-buthyl-9,10-diethoxyanthracene, 2,3-dimethyl-9,10-diethoxyanthracene, 9-ethoxy-10-methylanthracene, 9,10-dipropoxyanthracene, 9,10-diisopropoxyanthracene, 9,10-diethoxyanthracene, 2-ethyl-9,10-dipropoxyanthracene, 2-tert-buthyl-9,10-dipropoxyanthracene, 2,3-dimethyl-9,10-dipropoxyanthracene, 9-isopropoxy-10-methylanthracene, 9,10-dibenzyloxyanthracene, 2-ethyl-9,10-dibenzyloxyanthracene, 2-tert-buthyl-9,10-dibenzyloxyanthracene, 2,3-dimethyl-9,10-dibenzyloxyanthracene, 9-benzyloxy-10-methylanthracene, 9,10-di-α-methylbenzyloxyanthracene, 2-ethyl-9,10-di-α-methylbenzyloxyanthracene, 2-tert-buthyl-9,10-di-α-methylbenzyloxyanthracene, 2,3-dimethyl-9,10-di-α-methylbenzyloxyanthracene, 9-(α-methylbenzyloxy)-10-methylanthracene, 9,10-diphenylanthracene, 9-methoxyanthracene, 9-ethoxyanthracene, 9-methylanthracene, 9-bromoanthracene, 9-methlthioanthracene, 9-ethlthioanthracene and the like}; pyrene; 1,2-benzanthracene; perylene; tetracene; coronene; respective kinds of thioxanthone {thioxanthone, 2-methylthioxanthone, 2-ethylthioxanthone, 2-chlorothioxanthone, 2-isopropylthioxanthone, 2,4-diethylthioxanthone, and the like}; respective kinds of phenothiazine and derivatives thereof {phenothiazine, N-methylphenothiazine, N-ethylphenothiazine, N-phenylphenothiazine, and the like}; xanthone; naphthalenes {1-naphthol, 2-naphthol, 1-methoxynaphthalene, 2-methoxynaphthalene, 1,4-dihydroxynaphthalene, 1,5-dihydroxynaphthalene, 1,6-dihydroxynaphthalene, 2,7-dihydroxynaphthalene, 2,7-dimethoxynaphthalene, 1,1'-thiobis(2-naphthol), 1,1'-bi(2-naphthol), 4-methoxy-1-naphthol, and the like}; ketones {dimethoxyacetophenone, diethoxyacetophenone, 2-hydroxy-2-methyl-1-phenylpropane-1-one, 4'-isopropyl-2-hydroxy-2-methylpropiophenone, 2-hydroxymethyl-2-methylpropiophenone, 2,2-dimethoxy-1,2-diphenylethane-1-on, p-dimethylaminoacetophenone, p-tert-buthyldichloroacetophenone, p-tert-buthyltrichloroacetophenone, p-azidebenzalacetophenone, 1-hydroxycyclohexylphenylketone, benzoin, benzoinmethylether, benzoinethylether, benzoinisopropylether, benzoin-n-buthylether, benzoin-iso-buthylether, 1-[4-(2-hydroxyethoxy)phenyl]-2-hydroxy-2-methyl-1-propane-1-on, benzophenone, methyl o-benzoilbenzoate, michler's ketone, 4,4'-bisdiethylaminobenzophenone, 4,4'-dichlorobenzophenone, 4-benzoyl-4'-methyldiphenyl sulfide, and the like}; carbazoles {N-phenylcarbazole, N-ethylcarbazole, poly-N-vinylcarbazole, N-glycidylcarbazole, and the like}; chrysenes {1,4-dimethoxychrysene, 1,4-diethoxychrysene, 1,4-dipropoxychrysene, 1,4-dibenzyloxychrysene, 1,4-di-α-methylbenzyloxychrysene, and the like}; phenanthrenes {9-hydroxyphenanthrene, 9-methoxyphenanthrene, 9-ethoxyphenanthrene, 9-benzyloxyphenanthrene, 9,10-dimethoxyphenanthrene, 9,10-diethoxyphenanthrene, 9,10-dipropoxyphenanthrene, 9,10-dibenzyloxyphenanthrene, 9,10-di-α-methylbenzyloxyphenanthrene, 9-hydroxy-10-methoxyphenanthrene, 9-hydroxy-10-ethoxyphenanthrene, and the like}, and the like.

When a sensitizer is contained, the content of the sensitizer is preferably from 1 to 300 parts by weight, more preferably from 5 to 200 parts by weight, based on 100 parts of the photoacid generator.

Known pigments and the like may be used as pigments, examples of which include inorganic pigments (such as titanium oxide, iron oxide, and carbon black) and organic pigments (such as azo pigments, cyanine pigments, phthalocyanine pigments, and quinacridone pigments).

When a pigment is contained, the content of the pigment is preferably from 0.5 to 400,000 parts by weight, more preferably from 10 to 150,000 parts by weight, based on 100 parts of the photoacid generator.

Known fillers and the like may be used as fillers, examples of which include fused silica, crystalline silica, calcium carbonate, aluminum oxide, aluminum hydroxide, zirconium oxide, magnesium carbonate, mica, talc, calcium silicate, lithium aluminum silicate, and the like.

When a filler is contained, the content of the filler is preferably from 50 to 600,000 parts by weight, more preferably 300 to 200,000 parts by weight, based on 100 parts of the photoacid generator.

Known electroconductive particles can be used as electroconductive particles, and metal particles of Ni, Ag, Au, Cu, Pd, Pb, Sn, Fe, Ni, Al and the like, and plated metal particles obtained by further plating the above-mentioned metal particles with a metal, plated resin particles obtained by plating resin particles with a metal, particles of a substance having conductivity such as carbon, or the like can be used.

When electroconductive particles are contained, the content of the electroconductive particles is preferably from 50 to 30000 parts by weight, more preferably from 100 to 20000 parts by weight, based on 100 parts of the photoacid generator.

Known antistatic agents and the like may be used as antistatic agents, examples of which include nonionic antistatic agents, anionic antistatic agents, cationic antistatic agents, ampholytic antistatic agents, and high molecular weight antistatic agents.

When an antistatic agent is contained, the content of the antistatic agent is preferably from 0.1 to 20,000 parts by weight, more preferably from 0.6 to 5,000 parts by weight, based on 100 parts of the photoacid generator.

Known flame retardants and the like may be used as flame retardants, examples of which include inorganic flame retardants {such as antimony trioxide, antimony pentoxide, tin oxide, tin hydroxide, molybdenum oxide, zinc borate, barium metaborate, red phosphorus, aluminum hydroxide, magnesium hydroxide, and calcium aluminate}; bromine flame retardants {such as tetrabromophthalic anhydride, hexabromobenzene, and decabromobiphenyl ether}; and phosphate flame retardants {such as tris(tribromophenyl) phosphate}.

When a flame retardant is contained, the content of the flame retardant is preferably from 0.5 to 40,000 parts by weight, more preferably from 5 to 10,000 parts by weight, based on 100 parts of the photoacid generator.

Known anti-foaming agents and the like may be used as anti-foaming agents, examples of which include alcoholic anti-foaming agents, metallic soap anti-foaming agents, phosphate anti-foaming agents, fatty acid ester anti-foaming agents, polyether anti-foaming agents, silicone anti-foaming agents, and mineral oil anti-foaming agents.

Known fluidity controlling agents and the like may be used as fluidity controlling agents, examples of which include hydrogenated castor oil, oxidized polyethylene, organic bentonite, colloidal silica, amide wax, metallic soap, and acrylic ester polymers.

Known light stabilizers and the like may be used as light stabilizers, examples of which include ultraviolet absorbing stabilizers {such as benzotriazole, benzophenone, salicylates, cyanoacrylates, and derivatives thereof}; radical scavenging stabilizers {such as hindered amines}; and quenching stabilizers {such as nickel complexes}.

Known antioxidants and the like may be used as antioxidants, examples of which include phenolic antioxidants (such as monophenolic, bisphenolic, and macromolecular phenolic antioxidants), sulfur-based antioxidants, and phosphorus-based antioxidants.

Known tackifiers and the like may be used as tackifiers, example of which include coupling agents, silane coupling agents, and titanium coupling agents.

Known ion scavenger and the like may be used as ion scavenger, examples of which include organoaluminum (such as alkoxyaluminum and phenoxyaluminum).

Known anti-coloring agents and the like may be used as anti-coloring agents, and antioxidants are generally effective, examples of which include phenolic antioxidants (such as monophenolic, bisphenolic, and macromolecular phenolic antioxidants), sulfur-based antioxidants, and phosphorus-based antioxidants.

When an anti-foaming agent, a fluidity controlling agent, a light stabilizer, an antioxidant, a tackifier, an ion scavenger, or an anti-coloring agent is contained, the content of each material is preferably from 0.1 to 20,000 parts by weight, more preferably from 0.5 to 5,000 parts by weight, based on 100 parts of the photoacid generator.

Any solvent that can be used to dissolve the cationic polymerizable compound or to control the viscosity of the energy ray-curable composition may be used as solvents, examples of which include those listed for the above photoacid generator.

When a solvent is contained, the content of the solvent is preferably from 50 to 2,000,000 parts by weight, more preferably from 200 to 500,000 parts by weight, based on 100 parts of the photoacid generator.

Examples of the nonreactive resin include polyester, polyvinyl acetate, polyvinyl chloride, polybutadiene, polycarbonate, polystyrene, polyvinyl ether, polyvinyl butyral, polybutene, hydrogenated styrene-butadiene block copolymers, copolymers of (meth)acrylic acid esters, and polyurethane. The number average molecular weight of these resins is preferably from 1,000 to 500,000, more preferably from 5,000 to 100,000 (the number average molecular weight is a value measured by a general method such as GPC).

When a nonreactive resin is contained, the content of the nonreactive resin is preferably from 5 to 400,000 parts by weight, more preferably from 50 to 150,000 parts by weight, based on 100 parts of the photoacid generator.

When a nonreactive resin is contained, it is preferably dissolved in advance in a solvent so that it can be easily dissolved in the cationic polymerizable compound or the like.

Known radically-polymerizable compounds and the like may be used as radically-polymerizable compounds {such as those described in "Photopolymer Handbook" edited by The Technical Association of Photopolymers, Japan (1989, Kogyo Chosakai Publishing, Co., Ltd.), "UV/EB Koka Gijutsu" (Technology of UV/EB Curing), edited by Sogo Gijutsu Center (1982, Sogo Gijutsu Center), "UV/EB Koka- Zairyo" (UV/EB Curable Materials), edited by RadTech Japan (1992, CMC), and "UV-Koka niokeru Koka-Furyo/Sogai-Genin to Sonotaisaku" (Causes of UV Curing Defects/Inhibition and Remedies Therefor), edited by TECHNICAL INFORMATION INSTITUTE (2003, TECHNICAL INFORMATION INSTITUTE CO., LTD.)}, examples of which include monofunctional monomers, bifunctional monomers, polyfunctional monomers, epoxy (meth)acrylate, polyester (meth)acrylate, and urethane (meth)acrylate.

When a radically-polymerizable compound is contained, the content of the radically-polymerizable compound is preferably from 5 to 400,000 parts by weight, more preferably from 50 to 150,000 parts by weight, based on 100 parts of the photoacid generator.

When a radically-polymerizable compound is contained, a radical polymerization initiator initiating polymerization with heat or light is preferably used so that the compound can be polymerized by radical polymerization.

Known radical polymerization initiators and the like may be used as radical polymerization initiators, examples of which include thermal radical polymerization initiators (such as organic peroxides and azo compounds) and photo-radical polymerization initiators (such as acetophenone-based initiators, benzophenone-based initiators, Michler's ketone-based initiators, benzoin-based initiators, thioxanthone-based initiators, and acylphosphine-based initiators.

When a radical polymerization initiator is contained, the content of the radical polymerization initiator is preferably from 0.01 to 20 parts by weight, more preferably from 0.1 to 10 parts by weight, based on 100 parts of the radically-polymerizable compound.

The curable composition of the invention may be prepared by uniformly mixing and dissolving the cationic polymerizable compound, the photoacid generator, and if necessary an optional additive(s) at room temperature (about 20 to 30° C.) or if necessary, under heating (about 40 to 90° C.), or by further kneading them with a triple-roll mill or the like.

The curable composition of the invention may be cured by irradiation with energy rays so that a cured product can be obtained.

The energy ray may be of any energy ray as long as it has an energy to induce the decomposition of the photoacid generator of the invention, preferred examples of which include energy rays in the ultraviolet to visible light region (wavelength: from about 100 to about 800 nm) obtained from a low pressure-, medium pressure-, high pressure-, or ultra high pressure-mercury lamp, a metal halide lamp, an LED lamp, a xenon lamp, a carbon arc lamp, a fluorescent lamp, a semiconductor solid-state laser, an argon laser, a He—Cd laser, a KrF excimer laser, an ArF excimer laser, or an $F_2$ laser. Radiations with a high energy, such as electron beams or X-rays may also be used as the energy rays.

While the energy ray irradiation time is influenced by the intensity of the energy rays or the permeability of the energy rays to the energy ray-curable composition, an energy ray exposure time of about 0.1 to 10 seconds is enough at room temperature (about 20 to 30° C.). However, if the permeability of the energy rays is low or if the thickness of the energy ray-curable composition is large, for example, it is sometimes preferred to spend more time. Most energy ray-curable compositions are cured by cationic polymerization in 0.1 seconds to several minutes after the irradiation with energy rays. If necessary, however, post-curing may be performed by heating at a temperature of room temperature (about 20 to 30° C.) to 250° C. for several seconds to several hours after the irradiation with energy rays.

Here, the base material is a material to be coated or filled with the curable composition of the present invention, and a known material can be appropriately used. Examples of the base material in the present invention include resin films such as PET films, polypropylene films and polyimide films, metal foils such as aluminum foils, substrates of glass, copper, aluminum and the like, devices, light emitting diode elements, transistors and integrated circuits, and also include elements or circuits formed on the substrates described above.

The photoacid generator of the invention, which can generate a strong acid upon irradiation with light, may also be used as a photoacid generator for known chemically amplified resist materials (such as those described in JP-A No. 2003-267968, JP-A No. 2003-261529, and JP-A No. 2002-193925).

Examples of the chemically amplified resist materials include (1) a two-component chemically amplified positive resist comprising, as essential ingredients, a photoacid generator and a resin that can be made soluble in an alkali developing solution by the action of an acid; (2) a three-component chemically amplified positive resist comprising, as essential ingredients, a resin soluble in an alkali developing solution, a dissolution inhibitor that can be made soluble in an alkali developing solution by the action of an acid, and a photoacid generator; and (3) a chemically amplified negative resist comprising, as essential ingredients, a resin soluble in an alkali developing solution, a crosslinking agent that can crosslink the resin to make the resin insoluble in an alkali developing solution when heated in the presence of an acid, and a photoacid generator.

EXAMPLES

Hereinafter, the present invention will be further described by reference to examples, but the present invention is not intended to be limited thereto. It should be noted that a part means a part by weight and % means % by weight unless otherwise stated.

(Production Example 1) Synthesis of a Mixture Containing 4-[(phenyl)sulfinyl]biphenyl and 4-(phenylthio)biphenyl Charged were 2.0 parts of 4-(phenylthio)biphenyl, 8.0 parts of acetonitrile, and 0.037 parts of sulfuric acid, in a reactor, and the mixture solution was heated to 50° C., and then added dropwise was 0.43 parts of an aqueous 30% hydrogen peroxide solution over 10 minutes. The mixture was then stirred at 65° C. for 30 minutes, and cooled to room temperature. Thereto was added 30 parts of dichloromethane, and washing by liquid-liquid separation was performed with 40 parts of ion-exchanged water until the pH became neutral. The dichloromethane layer was transferred to a rotary evaporator, and the solvent was removed by distillation, so that a mixture containing 55% of 4-[(phenyl)sulfinyl]biphenyl and 45% of 4-(phenylthio) biphenyl was obtained. The product was isolated by column chromatography (eluent: ethyl acetate/hexane=1/1 in volume ratio) and then identified by $^1$H-NMR. The content was calculated from the peak area ratio obtained by HPLC analysis of the mixture.

(Production Example 2) Synthesis of a Mixture Containing 4-[(2-methylphenyl)sulfinyl]biphenyl and 4-[(2-methylphenyl)thio]biphenyl A mixture containing 51% of 4-[(2-methylphenyl)sulfinyl]biphenyl and 49% of 4-[(2-methylphenyl)thio]biphenyl was obtained as in Production Example 1, except that 2.0 parts of 4-(phenylthio)biphenyl was replaced with 2.1 parts of 4-[(2-methylphenyl)thio]biphenyl. The product was isolated by column chromatography (eluent: ethyl acetate/hexane=1/1 in volume ratio) and then identified by $^1$H-NMR. The content was calculated from the peak area ratio obtained by HPLC analysis of the mixture.

(Production Example 3) Synthesis of a Mixture Containing 4-[(2-methoxyphenyl)sulfinyl]biphenyl and 4-[(2-methoxyphenyl)thio]biphenyl A mixture containing 51% of 4-[(2-methoxyphenyl)sulfinyl]biphenyl and 49% of 4-[(2-methoxyphenyl)thio]biphenyl was obtained as in Production Example 1, except that 2.0 parts of 4-(phenylthio)biphenyl was replaced with 2.2 parts of 4-[(2-methoxyphenyl)thio]biphenyl. The product was isolated by column chromatography (eluent: ethyl acetate/hexane=1/1 in volume ratio) and then identified by $^1$H-NMR. The content was calculated from the peak area ratio obtained by HPLC analysis of the mixture.

(Production Example 4) Synthesis of a Mixture Containing [4-(phenoxy)phenyl]phenylsulfide and [4-(phenoxy)phenyl]phenylsulfoxide A mixture containing 39% of [4-(phenoxy)phenyl]phenylsulfide and 61% of [4-(phenoxy)phenyl]phenylsulfoxide was obtained as in Production Example 1, except that 2.0 parts of 4-(phenylthio)biphenyl was replaced with 2.0 parts of [4-(phenoxy)phenyl]phenylsulfide, and 0.43 parts of an aqueous 30% hydrogen peroxide solution was replaced with 0.49 parts of an aqueous 30% hydrogen peroxide solution. The product was isolated by column chromatography (eluent: ethyl acetate/hexane=1/1 in volume ratio) and then identified by $^1$H-NMR. The content was calculated from the peak area ratio obtained by HPLC analysis of the mixture.

(Production Example 5) Synthesis of a Mixture Containing [4-(phenoxy)phenyl](2-methylphenyl) sulfide and [4-(phenoxy)phenyl](2-methylphenyl) sulfoxide A mixture containing 42% of [4-(phenoxy)phenyl](2-methylphenyl)sulfide and 58% of [4-(phenoxy)phenyl](2-methylphenyl)sulfoxide was obtained as in Production Example 1, except that 2.0 parts of 4-(phenylthio) biphenyl was replaced with 2.1 parts of [4-(phenoxy)phenyl](2-methylphenyl) sulfide, and 0.43 parts of an aqueous 30% hydrogen peroxide solution was replaced with 0.46 parts of an aqueous 30% hydrogen peroxide solution. The product was isolated by column chromatography (eluent: ethyl acetate/hexane=1/1 in volume ratio) and then identified by $^1$H-NMR. The content was calculated from the peak area ratio obtained by HPLC analysis of the mixture.

(Production Example 6) Synthesis of a Mixture Containing [4-(phenoxy)phenyl](2-methoxyphenyl) sulfide and [4-(phenoxy)phenyl](2-methoxyphenyl) sulfoxide A mixture containing 42% of [4-(phenoxy)phenyl](2-methoxyphenyl)sulfide and 58% of [4-(phenoxy)phenyl](2-methoxyphenyl)sulfoxide was obtained as in Production Example 1, except that 2.0 parts of 4-(phenylthio)biphenyl was replaced with 2.22 parts of [4-(phenoxy)phenyl](2-methoxyphenyl)sulfide, and 0.43 parts of an aqueous 30% hydrogen peroxide solution was replaced with 0.46 parts of an aqueous 30% hydrogen peroxide solution. The product was isolated by column chromatography (eluent: ethyl acetate/hexane=1/1 in volume ratio) and then identified by $^1$H-NMR. The content was calculated from the peak area ratio obtained by HPLC analysis of the mixture.

(Production Example 7) Synthesis of a Mixture Containing [4-(trimethylsilyl)phenyl]phenylsulfide and [4-(trimethylsilyl)phenyl]phenylsulfoxide A mixture containing 48.5% of [4-(trimethylsilyl)phenyl]phenylsulfide and 51.5% of [4-(trimethylsilyl)phenyl]phenylsulfoxide was obtained as in Production Example 1, except that 2.0 parts of 4-(phenylthio) biphenyl was replaced with 2.0 parts of [4-(trimethylsilyl)phenyl]phenylsulfide, and 0.43 parts of an aqueous 30% hydrogen peroxide solution was replaced with 0.44 parts of an aqueous 30% hydrogen peroxide solution. The product was isolated by column chromatography (eluent: ethyl acetate/hexane=1/1 in volume ratio) and then identified by $^1$H-NMR. The content was calculated from the peak area ratio obtained by HPLC analysis of the mixture.

(Production Example 8) Synthesis of a Mixture Containing [4-(trimethylsilyl)phenyl](2-methylphenyl)sulfide and [4-(trimethylsilyl)phenyl](2-methylphenyl)sulfoxide A mixture containing 49% of [4-(trimethylsilyl)phenyl](2-methylphenyl)sulfide and 51% of [4-(trimethylsilyl)phenyl](2-methylphenyl)sulfoxide was obtained as in Production Example 1, except that 2.0 parts of 4-(phenylthio) biphenyl was replaced with 2.1 parts of [4-(trimethylsilyl)phenyl](2-methylphenyl)sulfide, and 0.43 parts of an aqueous 30% hydrogen peroxide solution was replaced with 0.44 parts of an aqueous 30% hydrogen peroxide solution. The product was isolated by column chromatography (eluent: ethyl acetate/hexane=1/1 in volume ratio) and then identified by $^1$H-NMR. The content was calculated from the peak area ratio obtained by HPLC analysis of the mixture.

(Production Example 9) Synthesis of a Mixture Containing [4-(triphenylsilyl)phenyl]phenylsulfide and [4-(triphenylsilyl)phenyl]phenylsulfoxide A mixture containing 49% of [4-(triphenylsilyl)phenyl]phenylsulfide and 51% of [4-(triphenylsilyl)phenyl]phenylsulfoxide was obtained as in Production Example 1, except that 2.0 parts of 4-(phenylthio)biphenyl was replaced with 2.0 parts of [4-(triphenylsilyl)phenyl]phenylsulfide, 0.037 parts of sulfuric acid was replaced with 0.022 parts of sulfuric acid, and 0.43 parts of an aqueous 30% hydrogen peroxide solution was replaced with 0.256 parts of an aqueous 30% hydrogen peroxide solution. The product was isolated by column chromatography (eluent: ethyl acetate/hexane=1/1 in volume ratio) and then identified by $^1$H-NMR. The content was calculated from the peak area ratio obtained by HPLC analysis of the mixture.

(Production Example 10) Synthesis of a Mixture Containing [4-(triphenylsilyl)phenyl](2-methylphenyl)sulfide and [4-(triphenylsilyl)phenyl](2-methylphenyl)sulfoxide A mixture containing 49% of [4-(triphenylsilyl)phenyl](2-methylphenyl)sulfide and 51% of [4-(triphenylsilyl)phenyl](2-methylphenyl)sulfoxide was obtained as in Production Example 1, except that 2.0 parts of 4-(phenylthio) biphenyl was replaced with 2.06 parts of [4-(triphenylsilyl) phenyl](2-methylphenyl)sulfide, 0.037 parts of sulfuric acid was replaced with 0.022 parts of sulfuric acid, and 0.43 parts of an aqueous 30% hydrogen peroxide solution was replaced with 0.256 parts of an aqueous 30% hydrogen peroxide solution. The product was isolated by column chromatography (eluent: ethyl acetate/hexane=1/1 in volume ratio) and then identified by $^1$H-NMR. The content was calculated from the peak area ratio obtained by HPLC analysis of the mixture.

(Production Example 11) Synthesis of a Mixture Containing 4-[(phenyl)sulfinyl]benzophenone and 4-(phenylthio)benzophenone A mixture containing 51% of 4-[(phenyl)sulfinyl]benzophenone and 49% of 4-(phenylthio)benzophenone was obtained as in Production Example 1, except that 2.0 parts of 4-(phenylthio)biphenyl was replaced with 2.0 parts of 4-(phenylthio)benzophenone, 8.0 parts of acetonitrile was replaced with 4.8 parts of acetonitrile, 0.037 parts of sulfuric acid was replaced with 0.034 parts of sulfuric acid, and 0.43 parts of an aqueous 30% hydrogen peroxide solution was replaced with 0.334 parts of an aqueous 35% hydrogen peroxide solution. The product was isolated by column chromatography (eluent: ethyl acetate/hexane=1/1 in volume ratio) and then identified by $^1$H-NMR. The content was calculated from the peak area ratio obtained by HPLC analysis of the mixture.

(Production Example 12) Synthesis of a Lithium tetrakis(pentafluorophenyl)gallate Charged were 360 parts of ultra-dehydrated diethyl ether and 30 parts of bromopentafluorobenzene in a 125 mL four-necked flask thoroughly dried under a nitrogen atmosphere, and the mixture was cooled to −78° C. using a dry ice/acetone bath. Added dropwise was 70 parts of a 2.5 mol/L n-butyllithium hexane solution over 10 minutes, and the mixture was then stirred at −78° C. for 30 minutes. Thereto was added dropwise 68 parts of a diethyl ether solution dissolved of 5 parts gallium (III) chloride over 10 minutes, and the mixture was stirred at −78° C. for 3 hours. The reaction liquid was stirred while being gradually returned to room temperature, and the reaction liquid was further stirred for 5 hours after being returned to room temperature. The precipitated solid was filtered, the reaction liquid was transferred to an evaporator, and the solvent was distilled off to obtain an off-white product. The product was washed with 50 parts of ultra-dehydrated hexane four times, and dried in vacuum overnight to obtain lithium tetrakis (pentafluorophenyl)gallate. The product was identified by $^{19}$F-NMR.

(Production Example 13) Synthesis of a Lithium tetrakis(3,5-bis(trifluoromethyl)phenyl)gallate A lithium tetrakis(3,5-bis(trifluoromethyl)phenyl)gallate was obtained as in Production Example 12, except that 30 parts of pentafluorobromobenzene was replaced with 35.6 parts of 1-bromo-3,5 bis(trifluoromethyl)benzene. The product was identified by $^{19}$F-NMR.

[Example 1] Synthesis of Photoacid Generator (A-1)

Charged were 2.0 parts of the mixture synthesized in Production Example 1 containing 55% of 4-[(phenyl)sulfinyl]biphenyl and 45% of 4-(phenylthio)biphenyl, 0.24 parts of 4-(phenylthio)biphenyl, 1.2 parts of acetic anhydride, 0.72 parts of trifluoromethanesulfonic acid, and 6.5 parts of acetonitrile in a reactor, and stirred at 60° C. for 2 hours. The reaction solution was cooled to room temperature and poured into 30 parts of ion-exchanged water. The mixture was extracted with 30 parts of dichloromethane, and the dichloromethane layer was washed with ion-exchanged water until the pH of the water layer became neutral. The dichloromethane layer was transferred to a rotary evaporator, and the solvent was removed by distillation, so that a product was obtained. Thereto was added 10 parts of ethyl acetate, and the product was dissolved in a water bath at 60° C. Subsequently, after 30 parts of hexane was added and stirred, the operation of allowing the mixture to stand for 30 minutes in a refrigerator (about 5° C.) and then removing the supernatant was performed twice to wash the product. The product was transferred to a rotary evaporator, and the solvent was removed by distillation, so that [4-(4-biphenylylthio)phenyl]-4-biphenylylphenylsulfonium triflate (triflate=trifluoromethanesulfonate anion) was obtained.
(Metathesis Process)

Poured were the triflate and 3.5 parts of lithium tetrakis (pentafluorophenyl)gallate into 27 parts of dichloromethane. Subsequently, the mixture was stirred at room temperature for 3 hours. After the dichloromethane layer was washed three times with ion-exchanged water by liquid-liquid separation, it was transferred to a rotary evaporator, and the solvent was removed by distillation, so that A-1 was obtained. The product was identified by $^1$H-NMR.

[Chemical Formula 15]

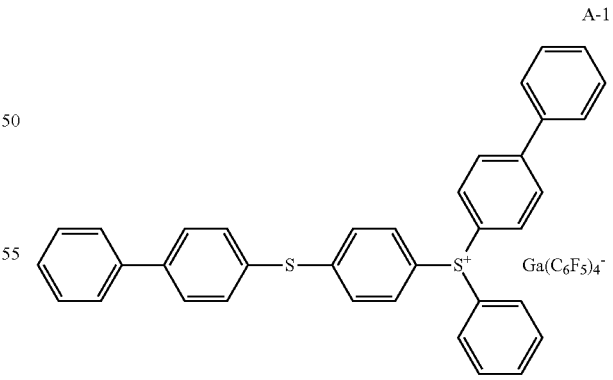

A-1

[Example 2] Synthesis of Photoacid Generator (A-2)

(A-2) was obtained as in Example 1, except that 3.5 parts of lithium tetrakis(pentafluorophenyl)gallate was replaced with 4.3 parts of lithium tetrakis(3,5-bis(trifluoromethyl)phenyl)gallate. The product was identified by ¹H-NMR.

[Chemical Formula 16]

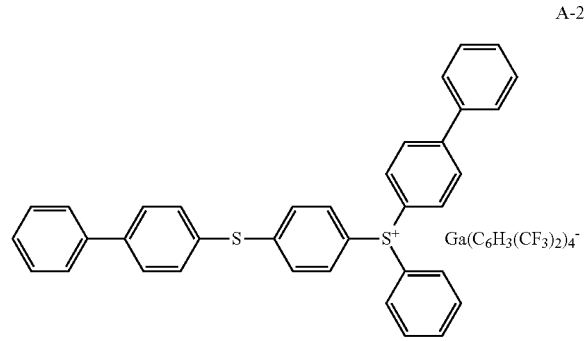

A-2

[Example 3] Synthesis of Photoacid Generator (A-3)

(A-3) was obtained as in Example 1, except that 2.0 parts of the mixture containing 55% of 4-[(phenyl)sulfinyl]biphenyl and 45% of 4-(phenylthio)biphenyl was replaced with 2.0 parts of the mixture synthesized in Production Example 2 containing 51% of 4-[(2-methylphenyl)sulfinyl]biphenyl and 49% of 4-[(2-methylphenyl)thio]biphenyl. The product was identified by ¹H-NMR.

[Chemical Formula 17]

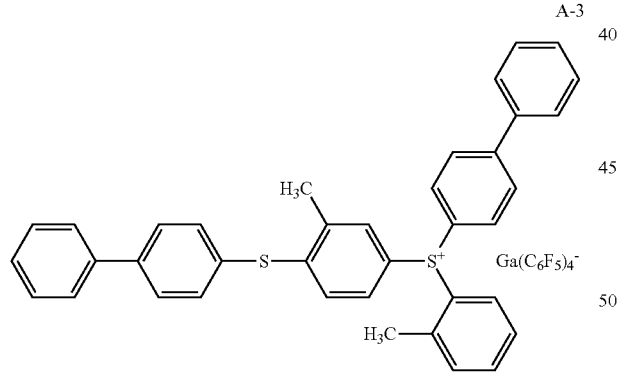

A-3

[Example 4] Synthesis of Photoacid Generator (A-4)

(A-4) was obtained as in Example 1, except that 2.0 parts of the mixture containing 55% of 4-[(phenyl)sulfinyl]biphenyl and 45% of 4-(phenylthio)biphenyl was replaced with 2.0 parts of the mixture synthesized in Production Example 2 containing 51% of 4-[(2-methylphenyl)sulfinyl]biphenyl and 49% of 4-[(2-methylphenyl)thio]biphenyl, and 3.5 parts of lithium tetrakis(pentafluorophenyl)gallate was replaced with 4.3 parts of lithium tetrakis(3,5-bis(trifluoromethyl)phenyl)gallate. The product was identified by ¹H-NMR.

[Chemical Formula 18]

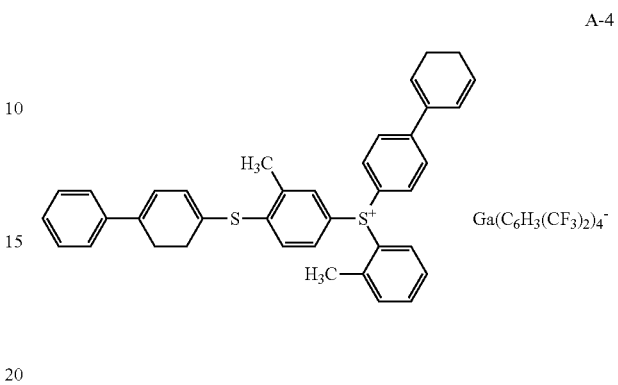

A-4

[Example 5] Synthesis of Photoacid Generator (A-5)

(A-5) was obtained as in Example 1, except that 2.0 parts of the mixture containing 55% of 4-[(phenyl)sulfinyl]biphenyl and 45% of 4-(phenylthio)biphenyl was replaced with 2.0 parts of the mixture synthesized in Production Example 3 containing 51% of 4-[(2-methoxyphenyl)sulfinyl]biphenyl and 49% of 4-[(2-methoxyphenyl)thio]biphenyl. The product was identified by ¹H-NMR.

[Chemical Formula 19]

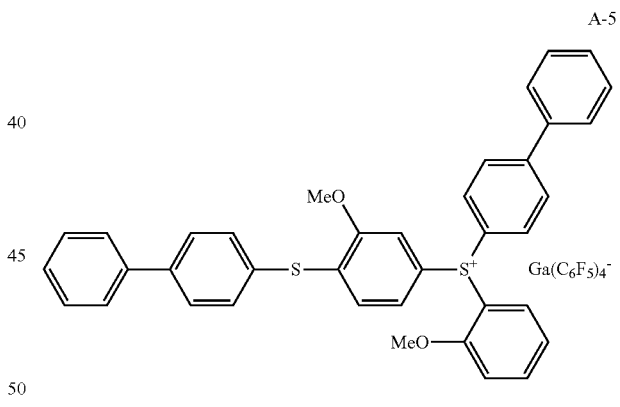

A-5

[Example 6] Synthesis of Photoacid Generator (A-6)

(A-6) was obtained as in Example 1, except that 2.0 parts of the mixture containing 55% of 4-[(phenyl)sulfinyl]biphenyl and 45% of 4-(phenylthio)biphenyl was replaced with 2.0 parts of the mixture synthesized in Production Example 3 containing 51% of 4-[(2-methoxyphenyl)sulfinyl]biphenyl and 49% of 4-[(2-methoxyphenyl)thio]biphenyl, and 3.5 parts of lithium tetrakis(pentafluorophenyl)gallate was replaced with 4.3 parts of lithium tetrakis(3,5-bis(trifluoromethyl)phenyl)gallate. The product was identified by ¹H-NMR.

[Chemical Formula 20]

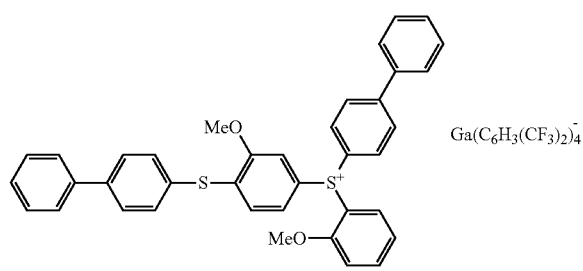

A-6

[Example 7] Synthesis of Photoacid Generator (A-7)

Dissolved was 5.2 parts of the mixture synthesized in Production Example 4 containing 49% of [4-(phenoxy)phenyl]phenylsulfide and 51% of [4-(phenoxy)phenyl]phenylsulfoxide in 15.5 parts of methanesulfonic acid. Then 2.8 parts of acetic anhydride was added dropwise at room temperature into the solution, and stirred at 60° C. for 6 hours. The reaction solution was cooled to room temperature and poured into 200 parts of ion-exchanged water. The mixture was extracted with 100 parts of dichloromethane, and the dichloromethane layer was washed with ion-exchanged water until the pH of the water layer became neutral. Then 8.8 parts of lithium tetrakis(pentafluorophenyl)gallate was added while stirring, and stirred at room temperature for 3 hours. The dichloromethane layer was washed three times with ion-exchanged water, and transferred to a rotary evaporator, and the solvent was removed by distillation, after that, the residue was washed with toluene/hexane solution, so that A-7 was obtained. The product was identified by $^1$H-NMR.

[Chemical Formula 21]

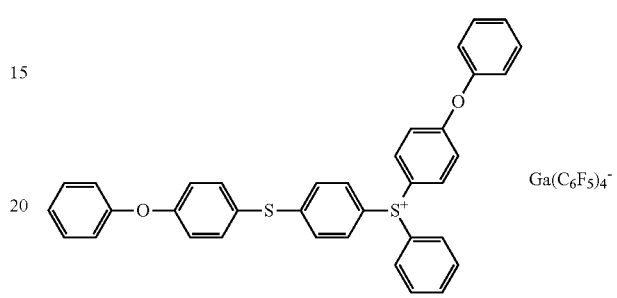

A-7

[Example 8] Synthesis of Photoacid Generator (A-8)

(A-8) was obtained as in Example 7, except that 8.8 parts of lithium tetrakis(pentafluorophenyl)gallate was replaced with 10.7 parts of lithium tetrakis(3,5-bis(trifluoromethyl)phenyl)gallate.

[Chemical Formula 22]

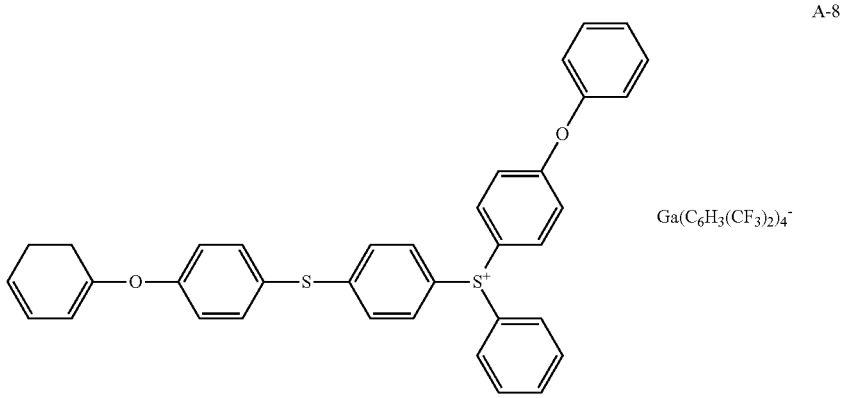

A-8

[Example 9] Synthesis of Photoacid Generator (A-9)

(A-9) was obtained as in Example 7, except that 5.2 parts of the mixture containing 49% of [4-(phenoxy)phenyl]phenylsulfide and 51% of [4-(phenoxy)phenyl]phenylsulfoxide was replaced with 5.2 parts of the mixture synthesized in Production Example 5 containing 42% of [4-(phenoxy)phenyl](2-methylphenyl) sulfide and 58% of [4-(phenoxy)phenyl](2-methylphenyl)sulfoxide. The product was identified by $^1$H-NMR.

[Chemical Formula 23]

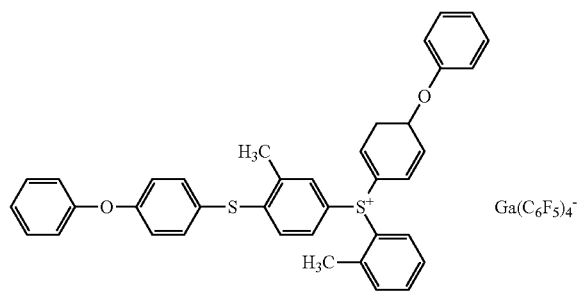

A-9

[Example 10] Synthesis of Photoacid Generator (A-10)

(A-10) was obtained as in Example 7, except that 5.2 parts of the mixture containing 49% of [4-(phenoxy)phenyl]phenylsulfide and 51% of [4-(phenoxy)phenyl]phenylsulfoxide was replaced with 5.2 parts of the mixture synthesized in Production Example 5 containing 42% of [4-(phenoxy)phenyl](2-methylphenyl) sulfide and 58% of [4-(phenoxy)phenyl](2-methylphenyl)sulfoxide, and 8.8 parts of lithium tetrakis(pentafluorophenyl)gallate was replaced with 10.7 parts of lithium tetrakis(3,5-bis(trifluoromethyl)phenyl)gallate. The product was identified by $^1$H-NMR.

[Chemical Formula 24]

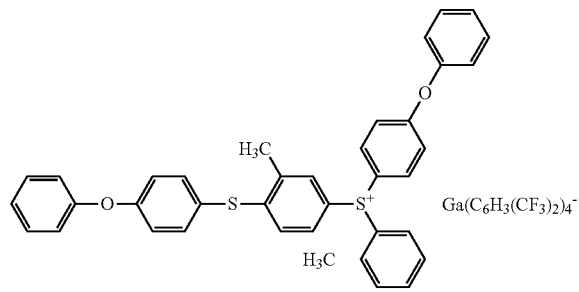

A-10

[Example 11] Synthesis of Photoacid Generator (A-11)

(A-11) was obtained as in Example 7, except that 5.2 parts of the mixture containing 49% of [4-(phenoxy)phenyl]phenylsulfide and 51% of [4-(phenoxy)phenyl]phenylsulfoxide was replaced with 5.2 parts of the mixture synthesized in Production Example 6 containing 42% of [4-(phenoxy)phenyl](2-methoxyphenyl)sulfide and 58% of [4-(phenoxy)phenyl](2-methoxyphenyl)sulfoxide. The product was identified by $^1$H-NMR.

[Chemical Formula 25]

A-11

[Example 12] Synthesis of Photoacid Generator (A-12)

(A-12) was obtained as in Example 7, except that 5.2 parts of the mixture containing 49% of [4-(phenoxy)phenyl]phenylsulfide and 51% of [4-(phenoxy)phenyl]phenylsulfoxide was replaced with 5.2 parts of the mixture synthesized in Production Example 6 containing 42% of [4-(phenoxy)phenyl](2-methoxyphenyl)sulfide and 58% of [4-(phenoxy)phenyl](2-methoxyphenyl)sulfoxide, and 8.8 parts of lithium tetrakis(pentafluorophenyl)gallate was replaced with 10.7 parts of lithium tetrakis(3,5-bis(trifluoromethyl)phenyl)gallate. The product was identified by $^1$H-NMR.

[Chemical Formula 26]

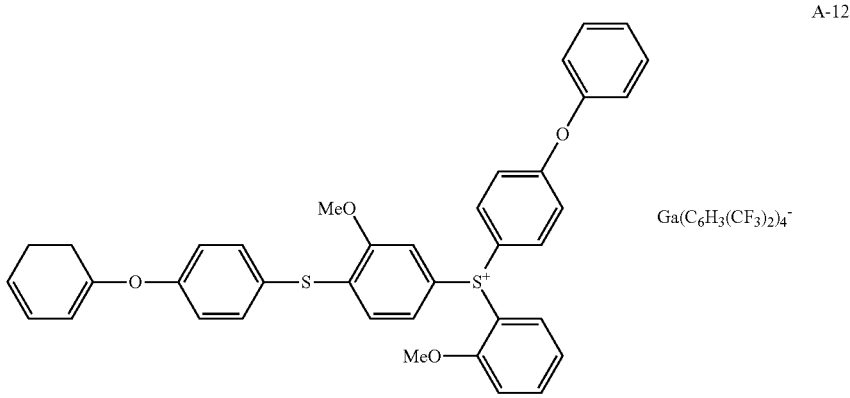

A-12

[Example 13] Synthesis of Photoacid Generator (A-13)

Charged were 4.8 parts of the mixture synthesized in Production Example 7 containing 48.5% of [4-(trimethylsilyl)phenyl]phenylsulfide and 51.5% of [4-(trimethylsilyl)phenyl]phenylsulfoxide and 23.3 parts of methanesulfonic acid in a reactor. Then 2.8 parts of acetic anhydride was added dropwise at room temperature into the solution, and stirred at 60° C. for 6 hours. The reaction solution was cooled to room temperature and poured into 200 parts of ion-exchanged water. The mixture was extracted with 100 parts of dichloromethane, and the dichloromethane layer was washed with ion-exchanged water until the pH of the water layer became neutral. Then 8.8 parts of lithium tetrakis(pentafluorophenyl)gallate was added while stirring, and stirred at room temperature for 3 hours. The dichloromethane layer was washed three times with ion-exchanged water by liquid-liquid separation, and transferred to a rotary evaporator, and the solvent was removed by distillation, after that, the residue was washed with toluene/hexane solution, so that A-13 was obtained. The product was identified by $^1$H-NMR.

[Chemical Formula 27]

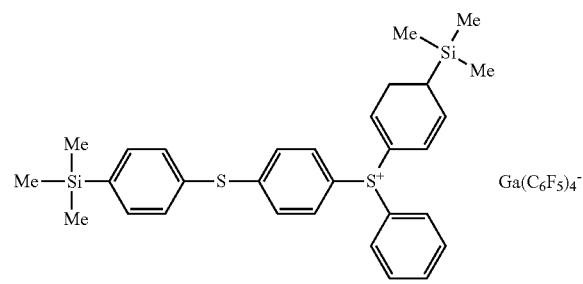

A-13

[Example 14] Synthesis of Photoacid Generator (A-14)

(A-14) was obtained as in Example 13, except that 8.8 parts of lithium tetrakis(pentafluorophenyl)gallate was replaced with 10.7 parts of lithium tetrakis(3,5-bis(trifluoromethyl)phenyl)gallate. The product was identified by $^1$H-NMR.

[Chemical Formula 28]

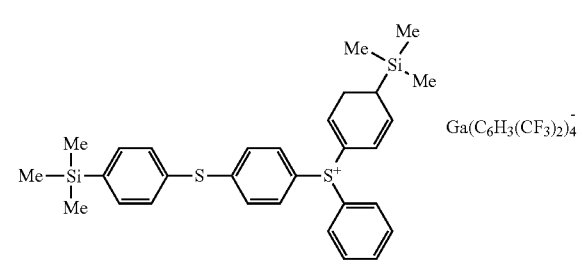

A-14

[Example 15] Synthesis of Photoacid Generator (A-15)

(A-15) was obtained as in Example 13, except that 4.8 parts of the mixture containing 48.5% of [4-(trimethylsilyl)phenyl]phenylsulfide and 51.5% of [4-(trimethylsilyl)phenyl]phenylsulfoxide was replaced with 5.1 parts of the mixture synthesized in Production Example 8 containing 49% of [4-(trimethylsilyl)phenyl](2-methylphenyl)sulfide and 51% of [4-(trimethylsilyl)phenyl](2-methylphenyl)sulfoxide. The product was identified by $^1$H-NMR.

[Chemical Formula 29]

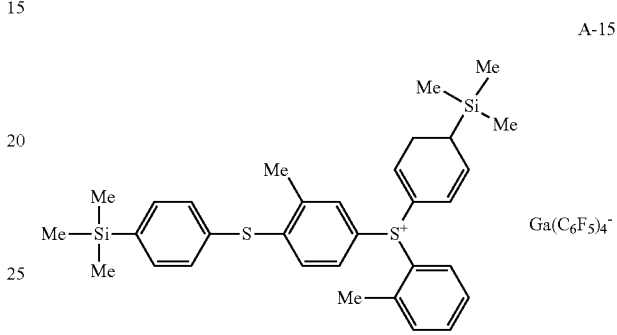

A-15

[Example 16] Synthesis of Photoacid Generator (A-16)

(A-16) was obtained as in Example 13, except that 4.8 parts of the mixture containing 48.5% of [4-(trimethylsilyl)phenyl]phenylsulfide and 51.5% of [4-(trimethylsilyl)phenyl]phenylsulfoxide was replaced with 5.1 parts of the mixture synthesized in Production Example 8 containing 49% of [4-(trimethylsilyl)phenyl](2-methylphenyl) sulfide and 51% of [4-(trimethylsilyl)phenyl](2-methylphenyl) sulfoxide, and 8.8 parts of lithium tetrakis(pentafluorophenyl)gallate was replaced with 10.7 parts of lithium tetrakis(3,5-bis(trifluoromethyl)phenyl)gallate. The product was identified by $^1$H-NMR.

[Chemical Formula 30]

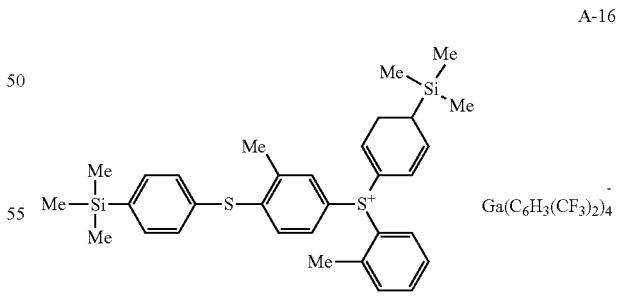

A-16

[Example 17] Synthesis of Photoacid Generator (A-17)

(A-17) was obtained as in Example 13, except that 4.8 parts of the mixture containing 48.5% of [4-(trimethylsilyl)phenyl]phenylsulfide and 51.5% of [4-(trimethylsilyl)phenyl]phenylsulfoxide was replaced with 8.2 parts of the mixture synthesized in Production Example 9 containing 49% of [4-(triphenylsilyl)phenyl]phenylsulfide and 51% of [4-(triphenylsilyl)phenyl]phenylsulfoxide, and 23.3 parts of methanesufonic acid was replaced with 38.8 parts of methanesufonic acid. The product was identified by $^1$H-NMR.

[Chemical Formula 31]

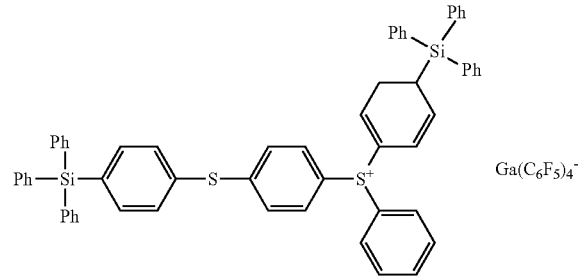

A-17

[Example 18] Synthesis of Photoacid Generator (A-18)

(A-18) was obtained as in Example 13, except that 4.8 parts of the mixture containing 48.5% of [4-(trimethylsilyl)phenyl]phenylsulfide and 51.5% of [4-(trimethylsilyl)phenyl]phenylsulfoxide was replaced with 8.2 parts of the mixture synthesized in Production Example 9 containing 49% of [4-(triphenylsilyl)phenyl]phenylsulfide and 51% of [4-(triphenylsilyl)phenyl]phenylsulfoxide, 23.3 parts of methanesufonic acid was replaced with 38.8 parts of methanesufonic acid, and 8.8 parts of lithium tetrakis(pentafluorophenyl)gallate was replaced with 10.7 parts of lithium tetrakis(3,5-bis(trifluoromethyl)phenyl)gallate. The product was identified by $^1$H-NMR.

[Chemical Formula 32]

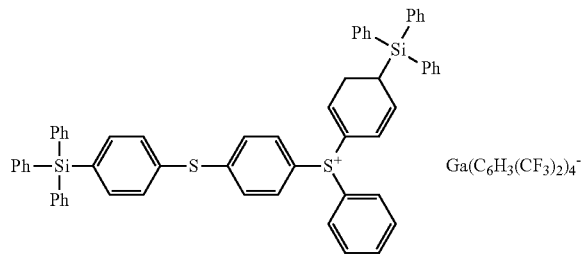

A-18

[Example 19] Synthesis of Photoacid Generator (A-19)

(A-19) was obtained as in Example 13, except that 4.8 parts of the mixture containing 48.5% of [4-(trimethylsilyl)phenyl]phenylsulfide and 51.5% of [4-(trimethylsilyl)phenyl]phenylsulfoxide was replaced with 8.5 parts of the mixture synthesized in Production Example 10 containing 49% of [4-(triphenylsilyl)phenyl](2-methylphenyl)sulfide and 51% of [4-(triphenylsilyl)phenyl](2-methylphenyl)sulfoxide, and 23.3 parts of methanesufonic acid was replaced with 38.8 parts of methanesufonic acid. The product was identified by $^1$H-NMR.

[Chemical Formula 33]

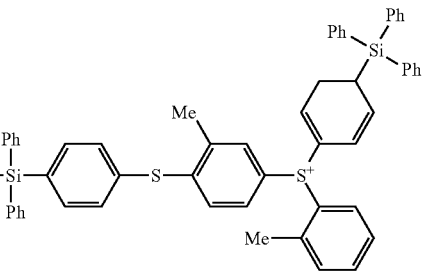

A-19

[Example 20] Synthesis of Photoacid Generator (A-20)

(A-20) was obtained as in Example 13, except that 4.8 parts of the mixture containing 48.5% of [4-(trimethylsilyl)phenyl]phenylsulfide and 51.5% of [4-(trimethylsilyl)phenyl]phenylsulfoxide was replaced with 8.5 parts of the mixture synthesized in Production Example 10 containing 49% of [4-(triphenylsilyl)phenyl](2-methylphenyl)sulfide and 51% of [4-(triphenylsilyl)phenyl](2-methylphenyl)sulfoxide, 23.3 parts of methanesufonic acid was replaced with 38.8 parts of methanesufonic acid, and 8.8 parts of lithium tetrakis(pentafluorophenyl)gallate was replaced with 10.7 parts of lithium tetrakis(3,5-bis(trifluoromethyl)phenyl)gallate. The product was identified by $^1$H-NMR.

[Chemical Formula 34]

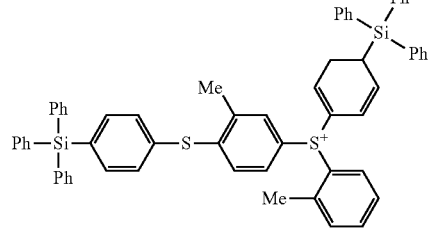

A-20

[Example 21] Synthesis of Photoacid Generator (A-21)

Charged were 10.3 parts of the mixture synthesized in Production Example 11 containing 51% of 4-[(phenyl)sulfinyl]benzophenone and 49% of 4-(phenylthio)benzophenone, 0.5 parts of 4-(phenylthio)benzophenone, 5.3 parts of acetic anhydride, 3.1 parts of trifluoromethanesulfonic acid, and 24.1 parts of acetonitrile in a reactor, and stirred at 60° C. for 2 hours. The reaction solution was cooled to room temperature and poured into 120 parts of ion-exchanged water. The mixture was extracted with 120 parts of dichloromethane, and the dichloromethane layer was washed with ion-exchanged water until the pH of the water layer became neutral. The dichloromethane layer was transferred to a rotary evaporator, and the solvent was removed by distillation, so that a product was obtained. Thereto was added 40 parts of ethyl acetate, and the product was dissolved in a water bath at 60° C. Subsequently, after 120 parts of hexane was added and stirred, the operation of allowing the mixture to stand for 30 minutes in a refrigerator (about 5° C.) and then removing the supernatant was performed twice to wash the product. The product was transferred to a rotary evaporator, and the solvent was removed by distillation, so that 4-benzoylphenyl-[4-(4-benzoylhenylylthio)phenyl]phenyl-sulfonium triflate(triflate=trifluoromethanesulfonate anion) was obtained.

(Metathesis Process)

Poured were the triflate and 15.4 parts of lithium tetrakis(pentafluorophenyl)gallate into 113 parts of dichloromethane. Subsequently, the mixture was stirred at room temperature for 3 hours. After the dichloromethane layer was washed three times with ion-exchanged water by liquid-liquid separation, it was transferred to a rotary evaporator, and the solvent was removed by distillation, so that A-21 was obtained. The product was identified by $^1$H-NMR.

[Chemical Formula 35]

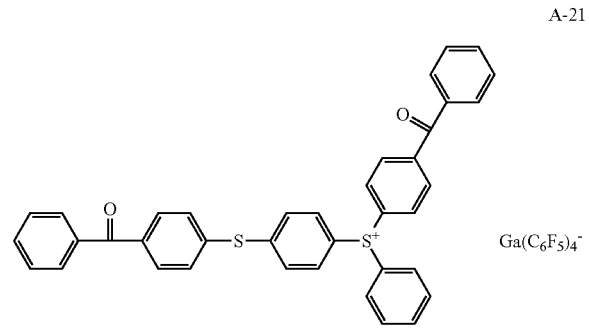

A-21

[Example 22] Synthesis of Photoacid Generator (A-22)

(A-22) was obtained as in Example 21, except that 15.4 parts of lithium tetrakis(pentafluorophenyl)gallate was replaced with 18.7 parts of lithium tetrakis(3,5-bis(trifluoromethyl)phenyl)gallate. The product was identified by $^1$H-NMR.

[Chemical Formula 36]

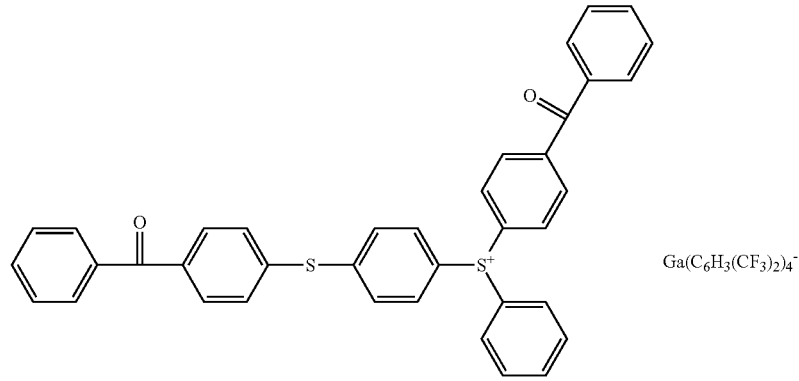

A-22

[Example 23] Synthesis of Photoacid Generator (A-23)

Charged were 12.5 parts of A-21 synthesized in Example 21, 82.9 parts of dehydrated dichloromethane, 0.03 parts of iron bromide, and 0.78 parts of bromine in a reactor, and stirred at room temperature for 4 hours. The reaction solution was transferred to a rotary evaporator, and the solvent was removed. Subsequently, 100 parts of dichloromethane was added, and the dichloromethane layer was washed with ion-exchanged water until the pH of the water layer became neutral. The dichloromethane layer was transferred to a rotary evaporator, and the solvent was removed, so that A-23 was obtained. The product was identified by $^1$H-NMR.

[Chemical Formula 37]

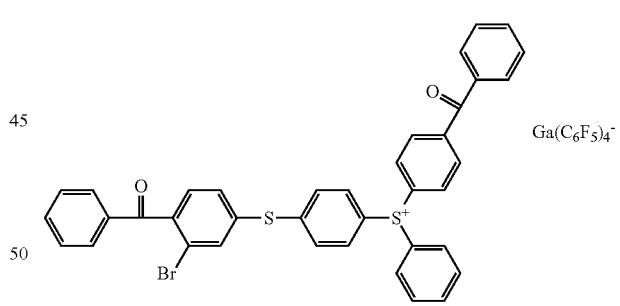

A-23

[Example 24] Synthesis of Photoacid Generator (A-24)

Charged were 14.1 parts of A-22 synthesized in Example 24, 82.9 parts of dehydrated dichloromethane, 0.03 parts of iron bromide, and 0.78 parts of bromine in a reactor, and stirred at room temperature for 4 hours. The reaction solution was transferred to a rotary evaporator, and the solvent was removed. Subsequently, 100 parts of dichloromethane was added, and the dichloromethane layer was washed with ion-exchanged water until the pH of the water layer became neutral. The dichloromethane layer was transferred to a rotary evaporator, and the solvent was removed, so that A-24 was obtained. The product was identified by $^1$H-NMR.

[Chemical Formula 38]

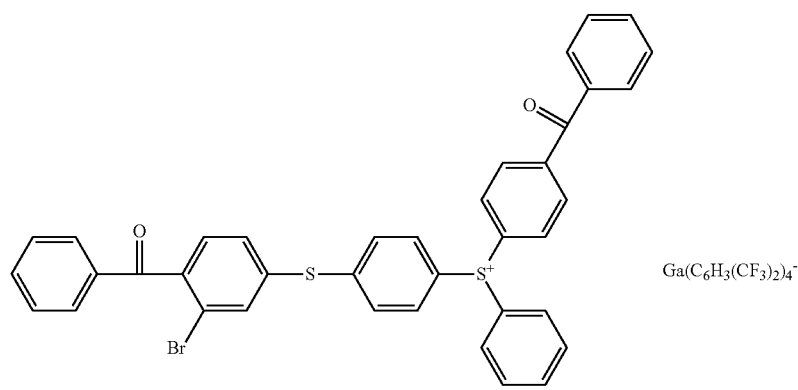

A-24

Ga(C₆H₃(CF₃)₂)₄⁻ rendered as $Ga(C_6H_3(CF_3)_2)_4^-$

[Example 25] Synthesis of Photoacid Generator (A-25)

89 parts of dichloromethane solution containing 32 parts of (4-phenylthio)phenyl diphenylsulfonium trifluoromethanesulfonate was added dropwise into the suspension mixed with 36.8 parts of aluminium chloride, 12.0 parts of acetic chloride, and 200 parts of dichloromethane while stirring and cooling as the temperature not beyond 10° C. After adding, the reaction solution was stirred at room temperature for 2 hours, and poured into 300 parts of cooled water while stirring. After removing the upper layer, the dichloromethane layer was washed with ion-exchanged water until the pH of the water layer became neutral. Then 5.5 parts of lithium tetrakis(pentafluorophenyl)gallate was added while stirring, and stirred at room temperature for 1 hours. The dichloromethane layer was washed three times with ion-exchanged water by liquid-liquid separation, and transferred to a rotary evaporator, and the solvent was removed, after that, the residue was washed with toluene/hexane solution, so that A-25 was obtained. The product was identified by $^1$H-NMR.

[Chemical Formula 39]

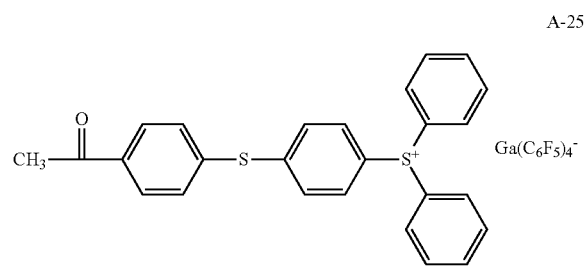

A-25

[Example 26] Synthesis of Photoacid Generator (A-26)

(A-26) was obtained as in Example 25, except that 5.5 parts of lithium tetrakis(pentafluorophenyl)gallate was replaced with 6.6 parts of lithium tetrakis(3,5-bis(trifluoromethyl)phenyl)gallate. The product was identified by $^1$H-NMR.

[Chemical Formula 40]

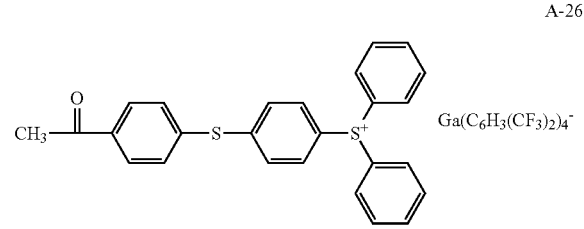

A-26

[Example 27] Synthesis of Photoacid Generator (A-27)

(A-27) was obtained as in Example 25, except that 12.0 parts of acetyl chloride was replaced with 21.7 parts of benzoyl chloride. The product was identified by $^1$H-NMR.

[Chemical Formula 41]

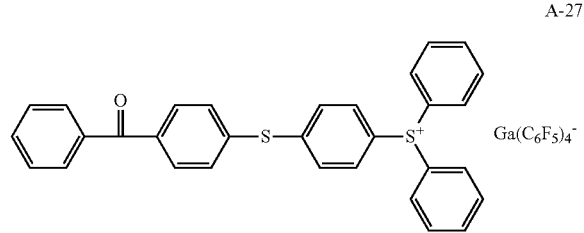

A-27

[Example 28] Synthesis of Photoacid Generator (A-28)

(A-28) was obtained as in Example 25, except that 12.0 parts of acetyl chloride was replaced with 21.7 parts of benzoyl chloride, and 5.5 parts of lithium tetrakis(pentafluorophenyl)gallate was replaced with 6.6 parts of lithium tetrakis(3,5-bis(trifluoromethyl)phenyl)gallate. The product was identified by $^1$H-NMR.

[Chemical Formula 42]

A-28

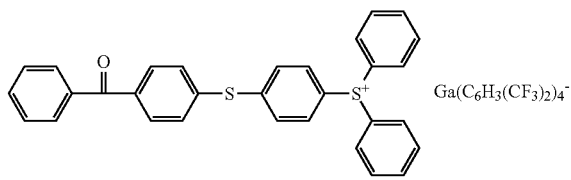

[Example 29] Synthesis of Photoacid Generator (A-29)

Charged were 4.3 parts of 2-(phenylthio)thioxanthone, 4.5 parts of 2-[(phenyl)sulfinyl]thioxanthone, 4.1 parts of acetic anhydride, and 110 parts of acetonitrile in a reactor. Then 2.4 parts of trifluoromethanesulfonic acid was added dropwise gradually at room temperature into the solution, and stirred at 40-45° C. for 1 hours. The reaction solution was cooled to room temperature and poured into 150 parts of ion-exchanged water. The mixture was extracted with 50 parts of dichloromethane, and the dichloromethane layer was washed with ion-exchanged water until the pH of the water layer became neutral. After the dichloromethane layer was transferred to a rotary evaporator, and the solvent was removed. The product was dispersed in toluene by ultrasonic cleaning device after adding 50 parts of toluene. The operation of allowing the dispersion to stand for 15 minutes and then removing the supernatant was performed three times to wash the solid product. The solid product was transferred to a rotary evaporator, and the solvent was removed, so that [4-(2-thioxanthonylthio)phenyl]phenyl-2-thioxanthonylsulfonium triflate(triflate=trifluoromethanesulfonate anion) was obtained.

(Metathesis Process)

Poured were the triflate and 10.9 parts of lithium tetrakis (pentafluorophenyl)gallate into 50 parts of dichloromethane. Subsequently, the mixture was stirred at room temperature for 3 hours. After the dichloromethane layer was washed three times with ion-exchanged water by liquid-liquid separation, it was transferred to a rotary evaporator, and the solvent was removed, so that A-29 was obtained. The product was identified by $^1$H-NMR.

[Chemical Formula 43]

A-29

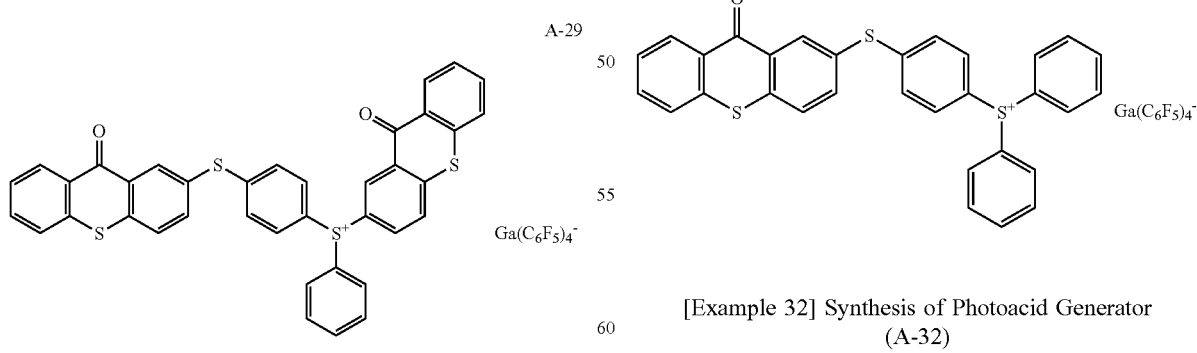

[Example 30] Synthesis of Photoacid Generator (A-30)

(A-30) was obtained as in Example 29, except that 10.9 parts of lithium tetrakis(pentafluorophenyl)gallate was replaced with 13.2 parts of lithium tetrakis(3,5-bis(trifluoromethyl)phenyl)gallate. The product was identified by $^1$H-NMR.

[Chemical Formula 44]

A-30

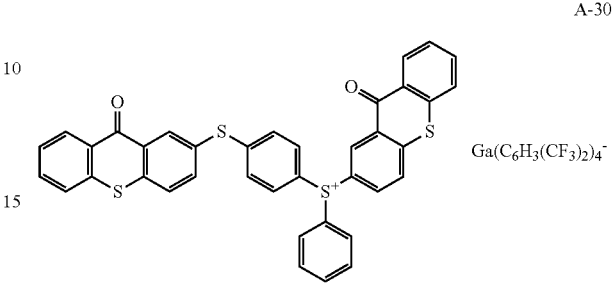

[Example 31] Synthesis of Photoacid Generator (A-31)

16.8 parts of 4-(phenylthio) phenyldiphenylsulfonium pentafluorophosphate was added gradually into the mixture of 2.0 parts of dithiosalicylic acid and 60 parts of sulfuric acid while stirring, and then was stirred for 1 hour. The reaction solution was poured into ion-exchanged water to precipitate the product. The precipitated solid was filtered, and the residue was washed with ion-exchanged water until the pH of the filtrate became neutral, so that solid product was obtained. The solid product was dissolved in 70 parts of dichloromethane, and 33.4 parts of lithium tetrakis(pentafluorophenyl)gallate was added to the dichloromethane solution, and then stirred at room temperature for 3 hours. The dichloromethane layer was washed three times with ion-exchanged water, and transferred to a rotary evaporator, and the solvent was removed, so that A-31 was obtained. The product was identified by $^1$H-NMR.

[Chemical Formula 45]

A-31

[Example 32] Synthesis of Photoacid Generator (A-32)

(A-32) was obtained as in Example 31, except that 33.4 parts of lithium tetrakis(pentafluorophenyl)gallate was replaced with 40.5 parts of lithium tetrakis(3,5-bis(trifluoromethyl)phenyl)gallate. The product was identified by $^1$H-NMR.

[Chemical Formula 46]

A-32

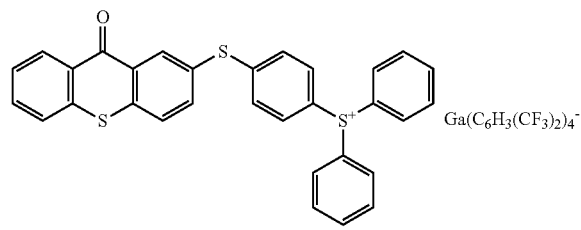

[Example 33] Synthesis of Photoacid Generator (A-33)

25 parts of dichloromethane solution containing 10 parts of (4-phenylthio)phenyl diphenylsulfonium trifluoromethanesulfonate was added dropwise into the suspension mixed with 7.7 parts of aluminium chloride, 2.9 parts of succinic anhydride, and 60 parts of dichloromethane while stirring and cooling as the temperature not beyond 10° C. After adding, the reaction solution was stirred at room temperature for 2 hours, poured into 300 parts of cooled water, stirred for 1 hour, and left to stand. After removing the upper layer, the dichloromethane layer was washed with ion-exchanged water until the pH of the water layer became neutral. Then 15.8 parts of lithium tetrakis(pentafluorophenyl)gallate was added while stirring, and stirred at room temperature for 1 hours. The dichloromethane layer was washed three times with ion-exchanged water by liquid-liquid separation, and transferred to a rotary evaporator, and the solvent was removed, after that, the residue was washed with toluene/hexane solution, so that A-33 was obtained. The product was identified by $^1$H-NMR.

[Chemical Formula 47]

A-33

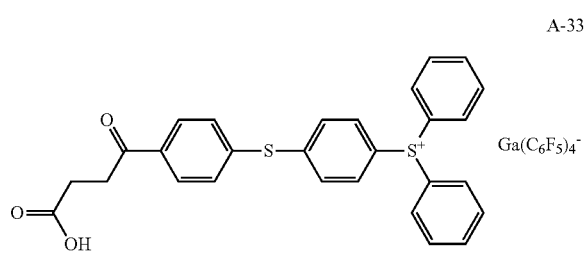

[Example 34] Synthesis of Photoacid Generator (A-34)

(A-34) was obtained as in Example 33, except that 15.8 parts of lithium tetrakis(pentafluorophenyl)gallate was replaced with 19.1 parts of lithium tetrakis(3,5-bis(trifluoromethyl)phenyl)gallate. The product was identified by $^1$H-NMR.

[Chemical Formula 48]

A-34

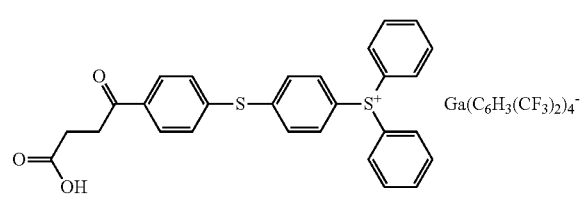

[Example 35] Synthesis of Photoacid Generator (A-35)

(A-35) was obtained as in Example 33, except that 7.7 parts of aluminium chloride was replaced with 10.1 parts of aluminium chloride and 2.9 parts of succinic anhydride was replaced with 4.3 parts of phthalic anhydride. The product was identified by $^1$H-NMR.

[Chemical Formula 49]

A-35

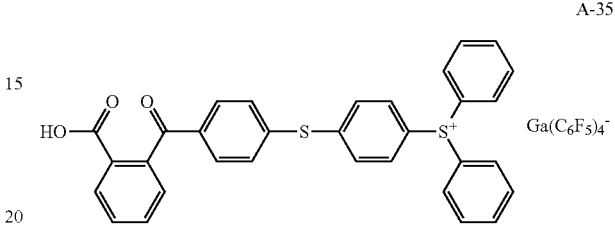

[Example 36] Synthesis of Photoacid Generator (A-36)

(A-36) was obtained as in Example 33, except that 7.7 parts of aluminium chloride was replaced with 10.1 parts of aluminium chloride, 2.9 parts of succinic anhydride was replaced with 4.3 parts of phthalic anhydride, and 15.8 parts of lithium tetrakis(pentafluorophenyl)gallate was replaced with 19.1 parts of lithium tetrakis(3,5-bis(trifluoromethyl)phenyl)gallate. The product was identified by $^1$H-NMR.

[Chemical Formula 50]

A-36

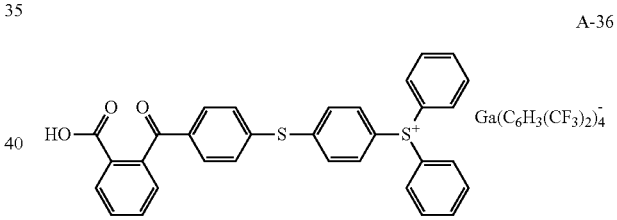

[Example 37] Synthesis of Photoacid Generator (A-37)

(A-37) was obtained as in Example 33, except that 7.7 parts of aluminium chloride was replaced with 15.4 parts of aluminium chloride and 2.9 parts of succinic anhydride was replaced with 5.7 parts of 2,3-naphthalenedicarboxylic anhydride. The product was identified by $^1$H-NMR.

[Chemical Formula 51]

A-37

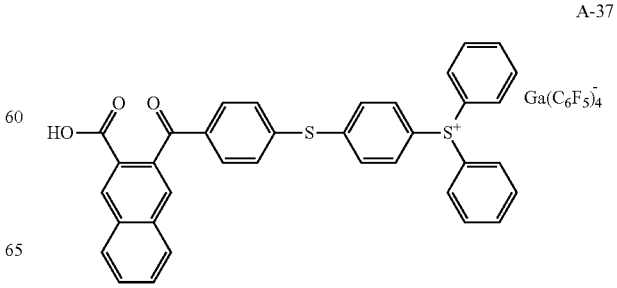

[Example 38] Synthesis of Photoacid Generator (A-38)

(A-38) was obtained as in Example 33, except that 7.7 parts of aluminium chloride was replaced with 15.4 parts of aluminium chloride, 2.9 parts of succinic anhydride was replaced with 5.7 parts of 2,3-naphthalenedicarboxylic anhydride, and 15.8 parts of lithium tetrakis(pentafluorophenyl)gallate was replaced with 19.1 parts of lithium tetrakis(3,5-bis(trifluoromethyl)phenyl)gallate. The product was identified by $^1$H-NMR.

[Chemical Formula 52]

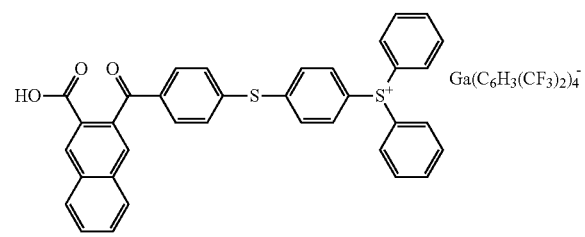

A-38

[Comparative Example 1] Synthesis of Photoacid Generator (A-39)

(A-39) was obtained as in Example 1, except that 3.5 parts of lithium tetrakis(pentafluorophenyl)gallate was replaced with 1.2 parts of potassium hexafluoroantimonate. The product was identified by $^1$H-NMR.

[Chemical Formula 53]

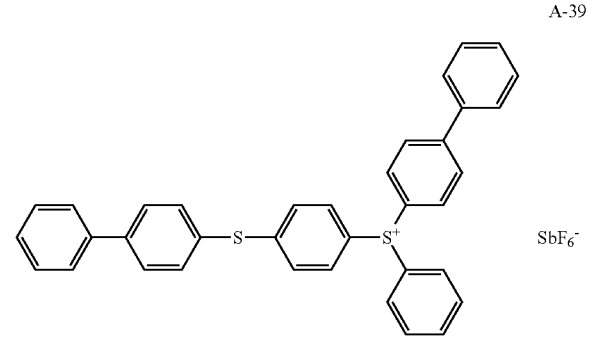

A-39

[Comparative Example 2] Synthesis of Photoacid Generator (A-40)

(A-40) was obtained as in Example 1, except that 3.5 parts of lithium tetrakis(pentafluorophenyl)gallate was replaced with 3.1 parts of potassium tetrakis(pentafluorophenyl)borate. The product was identified by $^1$H-NMR.

[Chemical Formula 54]

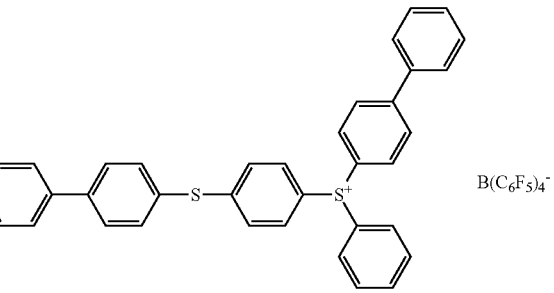

A-40

[Comparative Example 3] Synthesis of Photoacid Generator (A-41)

(A-41) was obtained as in Example 1, except that 3.5 parts of lithium tetrakis(pentafluorophenyl)gallate was replaced with 0.8 parts of potassium hexafluorophosphate. The product was identified by $^1$H-NMR.

[Chemical Formula 55]

A-41

[Evaluation]
(Preparation of Curable Composition)

The photoacid generator of the present invention and comparative compounds, an epoxide (3,4-epoxycyclohexylmethyl-3,4-epoxycyclohexane carboxylate, CELLOXIDE 2021 P manufactured by Daicel Chemical Industries, Ltd.) as a cationic polymerizable compound and bisphenol A (4,4'-(propane-2,2-diyl)diphenol manufactured by Idemitsu Kosan Co., Ltd) were uniformly mixed in an amount formulated as shown in Table 1 to prepare each of curable compositions 1 to 38 of the present invention and comparative curable compositions 39 to 41.

TABLE 1

| No. | photoacid generator | Amount of photoacid generator formulated | Epoxide | Bisphenol A |
|---|---|---|---|---|
| 1 | A-1 | 2 | 100 | 5 |
| 2 | A-2 | 2 | 100 | 5 |
| 3 | A-3 | 2 | 100 | 5 |
| 4 | A-4 | 2 | 100 | 5 |
| 5 | A-5 | 2 | 100 | 5 |
| 6 | A-6 | 2 | 100 | 5 |

TABLE 1-continued

| No. | photoacid generator | Amount of photoacid generator formulated | Epoxide | Bisphenol A |
|---|---|---|---|---|
| 7 | A-7 | 2 | 100 | 5 |
| 8 | A-8 | 2 | 100 | 5 |
| 9 | A-9 | 2 | 100 | 5 |
| 10 | A-10 | 2 | 100 | 5 |
| 11 | A-11 | 2 | 100 | 5 |
| 12 | A-12 | 2 | 100 | 5 |
| 13 | A-13 | 2 | 100 | 5 |
| 14 | A-14 | 2 | 100 | 5 |
| 15 | A-15 | 2 | 100 | 5 |
| 16 | A-16 | 2 | 100 | 5 |
| 17 | A-17 | 2 | 100 | 5 |
| 18 | A-18 | 2 | 100 | 5 |
| 19 | A-19 | 2 | 100 | 5 |
| 20 | A-20 | 2 | 100 | 5 |
| 21 | A-21 | 2 | 100 | 5 |
| 22 | A-22 | 2 | 100 | 5 |
| 23 | A-23 | 2 | 100 | 5 |
| 24 | A-24 | 2 | 100 | 5 |
| 25 | A-25 | 2 | 100 | 5 |
| 26 | A-26 | 2 | 100 | 5 |
| 27 | A-27 | 2 | 100 | 5 |
| 28 | A-28 | 2 | 100 | 5 |
| 29 | A-29 | 2 | 100 | 5 |
| 30 | A-30 | 2 | 100 | 5 |
| 31 | A-31 | 2 | 100 | 5 |
| 32 | A-32 | 2 | 100 | 5 |
| 33 | A-33 | 2 | 100 | 5 |
| 34 | A-34 | 2 | 100 | 5 |
| 35 | A-35 | 2 | 100 | 5 |
| 36 | A-36 | 2 | 100 | 5 |
| 37 | A-37 | 2 | 100 | 5 |
| 38 | A-38 | 2 | 100 | 5 |
| 39 | A-39 | 2 | 100 | 5 |
| 40 | A-40 | 2 | 100 | 5 |
| 41 | A-41 | 2 | 100 | 5 |

<Photosensitivity (Photo-Curability) Evaluation>

The curable compositions 1 to 38 of the present invention and comparative curable compositions 39 to 41 obtained above were applied to a polyethylene terephthalate (PET) film using an applicator (40 μm). Using an ultraviolet irradiator, the PET film was irradiated with ultraviolet light whose wavelength was restricted with filters. The filters used were 365 Filter (manufactured by EYE GRAPHICS Co., Ltd., a filter for cutting off light with wavelengths of less than 365 nm). Forty minutes after the irradiation, the pencil hardness (JIS K 5600-5-4: 1999) of the coating film hardness was measured and evaluated according to the criteria below (the coating film had a thickness of about 40 μm after the curing).

(Evaluation Criteria)

⊙: The pencil hardness is 2H or higher.

○: The pencil hardness is from H to B.

Δ: The pencil hardness is from 2B to 4B.

x: Due to liquidness or tackiness, it is not possible to measure the pencil hardness.

(Ultraviolet Light Irradiation Conditions)

Ultraviolet ray irradiator: belt conveyor-type UV irradiator (manufactured by EYE GRAPHICS Co., Ltd.)

Lamp: 1.5 kW high-pressure mercury lamp

Filter: 365 Filter (manufactured by EYE GRAPHICS Co., Ltd.)

Irradiance (measured with a 365 nm head photometer): 100 mW/cm$^2$

Integral light dose (measured with a 365 nm head photometer): 300 mJ/cm$^2$

<Heat Resistance (Yellowing) Test>

The compositions obtained as described above were applied onto a slide glass with a thickness of 40 μm by an applicator. Using an ultraviolet irradiator, the above-mentioned coated slide glass was irradiated with ultraviolet light.

(Ultraviolet Light Irradiation Conditions)

Ultraviolet ray irradiator: belt conveyor-type UV irradiator (manufactured by EYE GRAPHICS Co., Ltd.)

Lamp: 1.5 kW high-pressure mercury lamp

Irradiance (measured with a 365 nm head photometer): 100 mW/cm$^2$

Integral light dose (measured with a 365 nm head photometer): 1000 mJ/cm$^2$

After the irradiation, the composition was cured at room temperature for 40 minutes, and then post-cured on a hot plate at 120° C. for 30 minutes to prepare a heat resistance test sample.

The sample was heated for 15 minutes on a hot plate controlled to a temperature of 240° C., and the color of the coating film was visually evaluated. Evaluation criteria are as follows.

(Evaluation Criteria)

⊙: Colorless (yellowing of coating film does not occur)

○: Pale yellow or yellow x: Brown

<Metal Errosion Test>

The compositions obtained as described above were applied onto Cu board with a thickness of 40 μm by an applicator. Using an ultraviolet irradiator, the above-mentioned Cu board was irradiated with ultraviolet light.

(Ultraviolet Light Irradiation Conditions)

Ultraviolet ray irradiator: belt conveyor-type UV irradiator (manufactured by EYE GRAPHICS Co., Ltd.)

Lamp: 1.5 kW high-pressure mercury lamp

Irradiance (measured with a 365 nm head photometer): 100 mW/cm$^2$

Integral light dose (measured with a 365 nm head photometer): 1000 mJ/cm$^2$

After the irradiation, the composition was post-cured on a hot plate at 120° C. for 15 minutes to prepare a metal errosion test sample.

The sample was left to stand for 720 hours under hot and humid condition of 80° C./85%, and then a metal errosion test was performed. The existence of metal errosion about the after-tested board was visually evaluated. Evaluation criteria are as follows.

(Evaluation Criteria)

⊙: The color change of the Cu board was not found entirely by visual test.

○: The color change of the Cu board was found slight by visual test.

Δ: The Cu board was seen slight black by visual test.

x: The Cu board was changed pitch black.

TABLE 2

| No. | Photo-Curability | Heat Resistance (Yellowing) | Metal Errosion Resistance |
|---|---|---|---|
| 1 | ⊙ | ⊙ | ⊙ |
| 2 | ⊙ | ⊙ | ⊙ |
| 3 | ⊙ | ⊙ | ⊙ |
| 4 | ⊙ | ⊙ | ⊙ |
| 5 | ⊙ | ⊙ | ⊙ |
| 6 | ⊙ | ⊙ | ⊙ |
| 7 | ⊙ | ⊙ | ⊙ |
| 8 | ⊙ | ⊙ | ⊙ |

TABLE 2-continued

| No. | Photo-Curability | Heat Resistance (Yellowing) | Metal Errosion Resistance |
|---|---|---|---|
| 9 | ☉ | ☉ | ☉ |
| 10 | ☉ | ☉ | ☉ |
| 11 | ☉ | ☉ | ☉ |
| 12 | ☉ | ☉ | ☉ |
| 13 | ☉ | ☉ | ☉ |
| 14 | ☉ | ☉ | ☉ |
| 15 | ☉ | ☉ | ☉ |
| 16 | ☉ | ☉ | ☉ |
| 17 | ☉ | ☉ | ☉ |
| 18 | ☉ | ☉ | ☉ |
| 19 | ☉ | ☉ | ☉ |
| 20 | ☉ | ☉ | ☉ |
| 21 | ☉ | ☉ | ☉ |
| 22 | ☉ | ☉ | ☉ |
| 23 | ☉ | ☉ | ☉ |
| 24 | ☉ | ☉ | ☉ |
| 25 | ☉ | ☉ | ☉ |
| 26 | ☉ | ☉ | ☉ |
| 27 | ☉ | ☉ | ☉ |
| 28 | ☉ | ☉ | ☉ |
| 29 | ☉ | ☉ | ☉ |
| 30 | ☉ | ☉ | ☉ |
| 31 | ☉ | ☉ | ☉ |
| 32 | ☉ | ☉ | ☉ |
| 33 | ☉ | ☉ | ☉ |
| 34 | ☉ | ☉ | ☉ |
| 35 | ☉ | ☉ | ☉ |
| 36 | ☉ | ☉ | ☉ |
| 37 | ☉ | ☉ | ☉ |
| 38 | ☉ | ☉ | ☉ |
| 39 | ☉ | x | x |
| 40 | ☉ | x | x |
| 41 | x | ☉ | x |

From the results in Tables 2, it is apparent that the curable composition containing a photoacid generator of the present invention are useful for members that are required to have optical properties, such as displays, optical waveguides and optical lenses, because favorable UV curability is exhibited, a cured product has high transparency (hardly turns yellow) after a heat resistance test, and has excellent metal errosion resistance.

INDUSTRIAL APPLICABILITY

The curable composition of the present invention is suitably used for paints, coating agents, various coating materials (hard coats, anti-fouling coating materials, anti-fogging coating materials, anti-corrosion coating materials, optical fibers and the like), back surface treatment agents for adhesive tapes, release coating materials of release sheets for adhesive labels (release papers, release plastic films, release metal foils and the like), printing plates, ink compositions for dental materials (dental formulations and dental composites), ink compositions, inkjet ink compositions, positive resists (for formation of connection terminals and wiring patterns in production of electronic components such as circuit boards, CSP and MEMS elements), resist films, liquid resists and negative resists (permanent film materials of surface protecting films, interlayer dielectric films, planarizing films for semiconductor elements, and transparent electrode for FPD (ITO, IZO, GZO)etc.), resists for MEMS, positive photosensitive materials, negative photosensitive materials, various adhesives (various temporary fixing agents for electronic components, adhesives for HDD, adhesives for pick-up lenses, adhesives for functional films for FPD (polarizing plates, antireflection films), insulator films for circuit pattern and semiconductor sealing, anisotropic conductive adhesives (ACA), anisotropic conductive films (ACF), anisotropic conductive pastes (ACP) and the like), holographic resins, FPD materials (color filters, black matrices, partition wall materials, photospacers, ribs, orientation films for liquid crystals, sealing agents for FPD and the like), optical members, molding materials (for building materials, optical components and lenses), casting materials, putty materials, glass fiber impregnating agents, fillers, sealing materials, chip sealants (flip chip and COF), sealants for package (CSP or BGA), photosemiconductor (LED) sealing materials, optical waveguide materials, nano-imprint materials, stereolithography materials, and micro-stereolithography materials.

The invention claimed is:
1. A sulfonium salt formed of a sulfonium cation selected from a group indicated by general formulas (1), (2), and (3) described below and a gallate anion represented by formula (a),

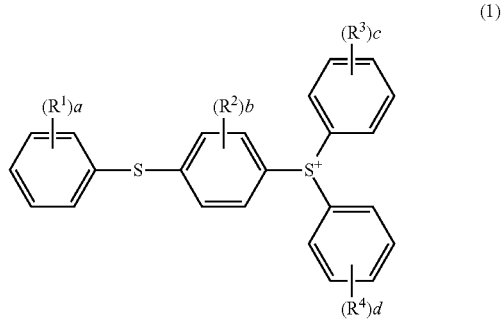

(1)

wherein formula (1), $R^1$ to $R^4$ each independently represent an alkyl group, an alkoxy group, an alkylcarbonyl group, an arylcarbonyl group, an aryl group, an aryloxy group, an optionally substituted silyl group, or a halogen atom; a, b, c, and d each represent the number of occurrences of each of $R^1$ to $R^4$; a represents an integer of 1 to 5; c and d represent an integer of 0 to 5; and b represents an integer of 0 to 4

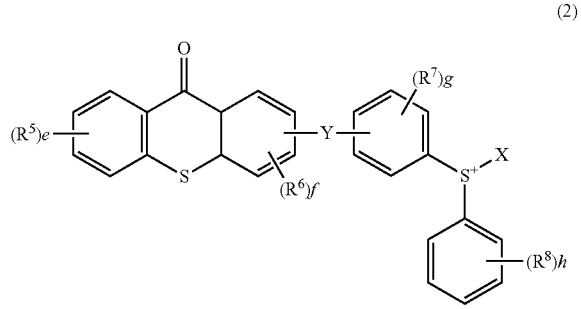

(2)

wherein formula (2), $R^5$ to $R^8$ each independently represent an alkyl group, or an alkoxy group; e, f, g, and h each represent the number of occurrences of each of $R^5$ to $R^8$; e and g represent an integer of 0 to 4; f represents an integer of 0 to 3; h represents an integer of 0 to 5; x represents an optionally substituted phenyl group or an optionally substituted thioxanthonyl group; Y represents —O—, —S—, —SO—, or —SO$_2$—,

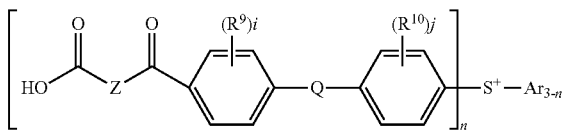

(3)

wherein formula (3), n represents an integer of 1 to 3; $R^9$ to $R^{10}$ each independently represent an alkyl group, or an alkoxy group; i and j each represent the number of occurrences of each of $R^9$ to $R^{10}$; i and j represent an integer of 0 to 4; Q represents single bond, —O— or —S—; Ar represents a phenyl group, and some of hydrogen atoms in the phenyl group may be substituted with an alkyl group, or an alkoxy group; Z represents an alkylene group having 2 to 6 carbon atoms or a phenylene group or naphthylene group,

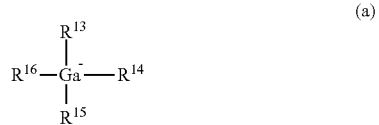

(a)

wherein $R^{13}$ to $R^{16}$ each independently represent a phenyl group or a perfluoroalkyl group, and some of hydrogen atoms in these groups may be substituted with a group selected from a perfluoroalkyl group, a perfluoroalkoxy group, a nitro group, a cyano group, an acyl group and a halogen atom.

2. The sulfonium salt according to claim 1, wherein in general formula (1), $R^1$ is a group selected from an alkylcarbonyl group, an aryl group, a silyl group, an arylcarbonyl group and an aryloxy group.

3. The sulfonium salt according to claim 1, wherein in general formula (1), $R^1$ is an aryl group or an alkylcarbonyl group.

4. The sulfonium salt according to claim 1, wherein in general formula (1), a is 1.

5. The sulfonium salt according to claim 1, wherein in general formula (1), a is 1 and b-d are 0.

6. The sulfonium salt according to claim 1, wherein in general formula (1), $R^1$ and $R^3$ are each independently a group selected from an alkylcarbonyl group, an aryl group, a silyl group, an arylcarbonyl group and an aryloxy group, a is 1 and c is 1.

7. The sulfonium salt according to claim 1, wherein in general formula (2), X is an optionally substituted thioxanthonyl group and Y is —S—.

8. The sulfonium salt according to claim 7, wherein in general formula (2), e, f, g and h are 0.

9. The sulfonium salt according to claim 1, wherein in general formula (3), n is 1, Q is —S—, i is 0, j is 0, Ar is phenyl group.

10. The sulfonium salt according to claim 1, wherein in general formula (a), $R^{13}$ to $R^{16}$ are a phenyl group substituted at least one selected from the group consisting of a perfluoroalkyl group and fluorine atom.

11. The sulfonium salt according to claim 1, wherein in general formula (a), a gallate anion represented by $[(R^{13})(R^{14})(R^{15})(R^{16})Ga]^-$ is $[Ga(C_6H_5)_4]^-$ or $[Ga((CF_3)_2C_6H_3)_4]^-$.

12. A photoacid generator, comprising the sulfonium salt according to claim 1.

13. An energy ray-curable composition, comprising the photoacid generator according to claim 12 and a cationic polymerizable compound.

14. A cured product obtained by curing the energy ray-curable composition according to claim 13.

15. The energy ray-curable composition according to claim 1, wherein the energy ray-curable composition has colorless in a heat resistance test, and no color change of a Cu board in a metal erosion test.

16. The energy ray-curable composition according to claim 1, wherein the energy ray-curable composition has colorless in a heat resistance test, and no color change of a Cu board in a metal erosion test,
wherein a sample of the heat resistance test is obtained by applying the energy ray-curable composition onto a slide glass with a thickness of 40 μm by an applicator; irradiating the energy ray-curable composition with an ultraviolet irradiator using a 1.5 kW high-pressure mercury lamp at an irradiance of 100 mW/cm² at an integral light dose of 1000 mJ/cm², to cure the energy ray-curable composition at room temperature for 40 minutes; and heating the slide glass,
Wherein a sample of the metal erosion test is obtained by applying the energy ray-curable composition onto a Cu board with a thickness of 40 μm by an applicator; irradiating the energy ray-curable composition with the ultraviolet irradiator; heating the energy ray-curable composition onto the Cu board; and leaving the energy ray-curable composition onto the Cu board for 720 hours under a condition of 80° C./85%.

* * * * *